United States Patent
Cory et al.

(10) Patent No.: US 10,603,504 B2
(45) Date of Patent: Mar. 31, 2020

(54) METHODS AND APPARATUS FOR ELECTRICALLY INDUCING NET MACRO-CURRENT ACROSS NEURONAL CELL MEMBRANES

(71) Applicant: Alacrity, Inc., San Jose, CA (US)

(72) Inventors: Philip C. Cory, Bozeman, MT (US); Steven P. Woodard, Cupertino, CA (US)

(73) Assignee: Alacrity, Inc., San Jose, CA (US)

( * ) Notice: Subject to any disclaimer, the term of this patent is extended or adjusted under 35 U.S.C. 154(b) by 0 days.

(21) Appl. No.: 16/126,768

(22) Filed: Sep. 10, 2018

(65) Prior Publication Data

US 2019/0076667 A1 Mar. 14, 2019

Related U.S. Application Data

(60) Provisional application No. 62/555,818, filed on Sep. 8, 2017.

(51) Int. Cl.
| | |
|---|---|
| *A61N 1/40* | (2006.01) |
| *A61B 5/00* | (2006.01) |
| *A61N 1/36* | (2006.01) |
| *A61N 1/04* | (2006.01) |
| *A61B 5/053* | (2006.01) |

(Continued)

(52) U.S. Cl.
CPC ............ *A61N 1/40* (2013.01); *A61B 5/04001* (2013.01); *A61B 5/053* (2013.01); *A61B 5/4836* (2013.01); *A61B 5/4893* (2013.01); *A61B 5/6877* (2013.01); *A61N 1/0456* (2013.01); *A61N 1/36021* (2013.01); *A61N 1/0534* (2013.01); *A61N 1/3706* (2013.01)

(58) Field of Classification Search
CPC ..... A61N 1/36021; A61N 1/40; A61N 1/0456
See application file for complete search history.

(56) References Cited

U.S. PATENT DOCUMENTS

| | | |
|---|---|---|
| 4,924,880 A | 5/1990 | O'Neill et al. |
| 5,117,826 A | 6/1992 | Bartelt et al. |

(Continued)

FOREIGN PATENT DOCUMENTS

| | | |
|---|---|---|
| AU | 2009217392 A1 | 9/2009 |
| EP | 1064047 A1 | 1/2001 |

(Continued)

OTHER PUBLICATIONS

International Search Report and Written Opinion of the International Searching Authority, for International Application No. PCT/US2018/050234, dated Apr. 23, 2019. 16 pages.

(Continued)

*Primary Examiner* — Alyssa M Alter
(74) *Attorney, Agent, or Firm* — The Marbury Law Group, PLLC

(57) ABSTRACT

Methods and devices are disclosed for inducing analgesia in a localized region of tissue. Inducing analgesia may be performed by identifying a nerve associated with the localized region, determining a resonant frequency for target neuronal cell membranes of the nerve, and generating a peripheral nerve blockade using the determined resonant frequency. The resonant frequency may be a frequency at which impedance of the nerve approaches a maximum.

18 Claims, 16 Drawing Sheets

(51) Int. Cl.
*A61B 5/04* (2006.01)
*A61N 1/37* (2006.01)
*A61N 1/05* (2006.01)

(56) References Cited

U.S. PATENT DOCUMENTS

| | | | |
|---|---|---|---|
| 5,782,874 | A | 7/1998 | Loos |
| 6,167,304 | A | 12/2000 | Loos |
| 7,326,181 | B2 | 2/2008 | Katims |
| 7,587,245 | B2 | 9/2009 | Kivlighan |
| 8,712,516 | B2 | 4/2014 | Cantatore |
| 8,788,042 | B2 | 7/2014 | Mercanzini et al. |
| 8,892,198 | B2 | 11/2014 | Bohorquez et al. |
| 8,996,115 | B2 | 3/2015 | Trier et al. |
| RE45,718 | E | 10/2015 | Kilgore et al. |
| 9,295,841 | B2 | 3/2016 | Fang et al. |
| 9,474,898 | B2 | 10/2016 | Gozani et al. |
| 9,550,068 | B2 | 1/2017 | Weinstock |
| 2003/0074039 | A1* | 4/2003 | Puskas .................. A61N 1/0517 607/118 |
| 2007/0073354 | A1 | 3/2007 | Knudson et al. |
| 2012/0118751 | A1 | 9/2012 | Cory |
| 2013/0035606 | A1 | 2/2013 | Wichner |
| 2013/0253365 | A1 | 9/2013 | Corsson et al. |
| 2014/0194949 | A1 | 7/2014 | Wichner |
| 2015/0224301 | A1 | 8/2015 | Durand et al. |
| 2016/0287875 | A1 | 10/2016 | Thacker et al. |
| 2017/0007151 | A1 | 1/2017 | Rutkove et al. |
| 2017/0050024 | A1 | 2/2017 | Bhadra et al. |
| 2017/0143969 | A1* | 5/2017 | Sarpeshkar ........ A61N 1/36125 |

FOREIGN PATENT DOCUMENTS

| | | |
|---|---|---|
| EP | 2379167 A1 | 10/2011 |
| EP | 2563466 A2 | 3/2013 |
| JP | 2016-005811 A | 1/2016 |
| KR | 10-2010-0083882 A | 7/2010 |
| WO | 2006044868 A1 | 4/2006 |
| WO | 2016/032929 A2 | 3/2016 |

OTHER PUBLICATIONS

Franke, et al., Abstract of "Direct Current Contamination of Kilohertz Frequency Alternating Current Waveforms", J. Neurosci Methods, pp. 74-83, (Jul. 30, 2014).

Sahin, et al., "Non-rectangular waveforms for neural stimulation with practical electrodes", IOP Publishing, J. Neural Eng. 4, pp. 227-233, (May 3, 2007).

Kilgore, "A Novel Waveform for Electrical Nerve Conduction Block", Orthopaedics, 2 pages, (May 31, 2004).

* cited by examiner

METHODS AND APPARATUS FOR ELECTRICALLY INDUCING NET MACRO-CURRENT ACROSS NEURONAL CELL MEMBRANES

RELATED APPLICATIONS

This application claims the benefit of priority to U.S. Provisional Application No. 62/555,818, entitled "Methods and Apparatus for Electrically Inducing Analgesia and Anesthesia" filed Sep. 8, 2017, the entire contents of which are hereby incorporated by reference.

BACKGROUND

The neuronal cell membrane comprises a phospholipid bilayer and numerous embedded ion channels traversing the membrane. Embedded proteins transport charged molecules altering the electrochemical gradient across the membrane. In response to a stimulus, a voltage differential across the membrane crosses a depolarization threshold, resulting in an action potential.

Numerous studies have established that the neuronal cell membrane displays the electrical characteristics of resistance (R), derived from embedded ion channels, and capacitance (C), derived from the phospholipid bilayer structure, as a parallel-RC circuit. The parallel-RC circuit equivalent circuit of all cell membranes, including neurons, uses the resistance and capacitance of the phospholipid bilayer. Nerves are preferential electrical current conduction pathways through tissue, and their presence in living tissue makes the tissue anisotropic to electrical current flow. This anisotropicity and phenomenological inductance of the neuronal cell membrane may be demonstrated using externally applied fields.

The impedance neurography developments based on this anisotropicity of nerve conduction pathways, in combination with methods to develop a transmembrane current flow, have led to insights regarding the neuronal cell membrane electrical responses. As a result, a wide range of clinical applications may be advanced.

SUMMARY

Systems, methods, and devices of various embodiments enable inducing analgesia in a localized region of tissue by identifying a nerve associated with the localized region, determining a resonant frequency for target neuronal cell membranes of the nerve, and generating a peripheral nerve blockade using the determined resonant frequency. In some embodiments, the resonant frequency may be a frequency at which impedance of the nerve approaches a maximum.

In some embodiments, determining a resonant frequency for target neuronal cell membranes may include applying, to at least one electrode, a periodic waveform over a range of frequencies, measuring impedance of the target neuronal cell membranes throughout the range of frequencies, and identifying a peak impedance. In some embodiments, the at least one electrode may be attached to a tissue surface in proximity to a section of the nerve.

In some embodiments, the resonant frequency for target neuronal cell membranes may be within a range of 2-3 kHz or 12-15 kHz. In some embodiments, generating the peripheral nerve blockade using the determined resonant frequency may include applying a fully-rectified, time-variant waveform to the at least one electrode to achieve a voltage gradient across target neuronal cell membranes, and applying a signal at an electrical resonant frequency of the target neuronal membranes to the at least one electrode. In some embodiments, the voltage gradient may drive a net macro-current across the target neuronal cell membranes. In some embodiments, at least one electrode may be within an array of a plurality of electrodes.

Systems, methods, and devices of various embodiments enable achieving a peripheral nerve blockade by attaching a plurality of electrodes to a tissue surface in proximity to a section of nerve, applying a fully-rectified, time-variant waveform to at least one of the plurality of electrodes to achieve a voltage gradient across target neuronal cell membranes, and applying an electrical signal at an electrical resonant frequency of the target neuronal membranes. In some embodiments, the voltage gradient may drive a net macro-current across the target neuronal cell membranes.

In some embodiments, the electrical resonant frequency may be a frequency at which impedance of the target neuronal membranes is maximized. Various embodiments may further include achieving a central enkephalinergic inhibition of ascending neuronal transmission by constructing a low frequency waveform using components of the electrical resonant frequency of the target neuronal membranes.

Various embodiments may further include determining the electrical resonant frequency by applying a periodic waveform to the plurality of electrodes over a range of frequencies, measuring impedance of the target neuronal cell membranes throughout the range, and identifying a peak impedance. In some embodiments, the range of frequencies is within 2-5 kHz. In some embodiments, the periodic waveform may be applied to each of the plurality of electrodes at increments selected from 250 Hz, 100 Hz, or 10 Hz. In some embodiments, the range of frequencies is within 12-15 kHz. In some embodiments, the periodic waveform may be applied to each of the plurality of electrodes at increments selected from 250 Hz, 100 Hz, or 10 Hz.

Systems, methods, and devices of various embodiments enable maintaining a net macro-current across target neuronal cell membranes within a section of a nerve by attaching at least one electrode to tissue in proximity to the section of the nerve, applying a fully-rectified, time-variant waveform to the at least one electrode such that charge is accumulated by capacitive tissue elements, and maintaining the fully-rectified, time-variant waveform for a number of cycles sufficient to achieve a voltage gradient across the membranes. In some embodiments, the voltage gradient results in a net macro-current across the membranes, and the electrical reactance of the membranes is altered. Systems, methods, and devices of various embodiments enable altering a transmembrane voltage gradient of target neurons by attaching a plurality of electrodes to the tissue of a patient in proximity to a section of nerve, and applying a fully-rectified, time-variant waveform to at least one of the plurality of electrodes to achieve a voltage gradient across membranes of the target neurons that results in a net macro-current across the membranes. In some embodiments, the resting transmembrane voltage gradient may be altered during the time that net macro-current is maintained across the membranes. In some embodiments, the fully-rectified, time-variant waveform may have a frequency of less than 3 kilohertz (kHz) such that the net macro-current across the membranes flows from outside the membranes of the target neurons to an axonal path within the nerve.

BRIEF DESCRIPTION OF THE DRAWINGS

The accompanying drawings, which are incorporated herein and constitute part of this specification, illustrate examples of various aspects, and together with the general description given above and the detailed description given below, serve to explain the features of the claims.

DETAILED DESCRIPTION OF INVENTION

Figure 1:
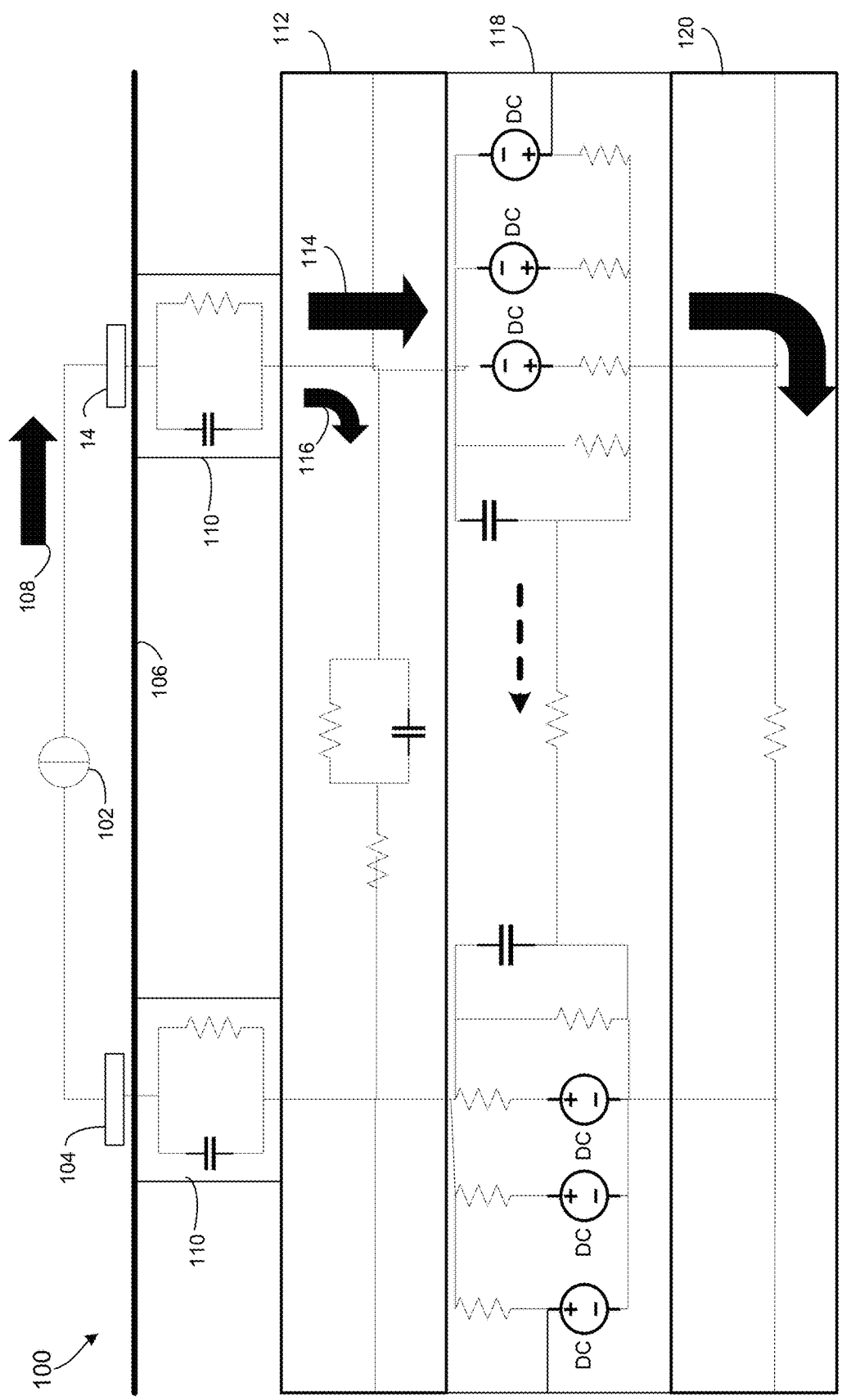
FIG. 1 is a cross-sectional schematic representation of tissue electrical equivalent circuits and a nerve electrical anisotropic pathway for current.

The various embodiments will be described in detail with reference to the accompanying drawings. Wherever possible, the same reference numbers will be used throughout the drawings to refer to the same or like parts. References made to particular examples and implementations are for illustrative purposes and are not intended to limit the scope of the claims.

The neuronal cell membrane, like all biological membranes, displays the electrical characteristics of resistance (R) and capacitance (C) as a parallel RC circuit. The resistance properties derive from the phospholipid bilayer structure of the membrane with imbedded ion channels while the capacitance properties are owed primarily to the phospholipid bilayer structure, with both properties functioning in parallel in the membrane. Although many studies over the years have shown the neuronal cell membrane to conform to this equivalent circuit, a previously unrecognized feature of the neuronal membrane equivalent circuit model is its dependence on the characteristics of the applied electrical field.

It is well-documented that the application of supra-threshold, periodic, time-variant current or voltage waveforms results in central nervous system inhibitory neuron release of enkephalins to reduce ascending transmission of nociceptive inputs from small diameter peripheral afferent nerves. This is largely attributed to low-frequency electrical nerve stimulation waveforms. Utilization of low amplitude, high-frequency waveforms in the kilohertz range is thought to block potassium channel function by the rapid oscillatory effect on the channel kinetics. However, while several studies have been performed using high frequency neuromodulation techniques, these experiments have had mixed results. This disparate understanding of the underlying mechanisms among researchers can be explained by electrical resonance of the nerve.

In electrical circuits, two opposing types of reactance that may exist are capacitive reactance and inductive reactance. At the resonant or critical frequency, the two reactances are equal in magnitude and 180 degrees apart in phase, causing the circuit to electrically oscillate. It is recognized that when applying a time-variant waveform to tissue where the voltage is not strictly biphasic, nor is the waveform forcibly returned to baseline (e.g., grounding) at its minimal values, the waveform will develop a progressive direct current (DC) offset voltage that plateaus after several waveform cycles have occurred. The number of waveform cycles seen before stabilization at a plateau value is dependent on both the ratio of the frequency of the applied waveform to the effective time constant of the tissue circuit as well as the use of controlled voltage or controlled current outputs. Since this offset voltage is a result of energy accumulation in conservative electrical elements of the tissue circuit, it may be referred to interchangeably herein as a "DC offset," "DC offset voltage," "charged-DC offset" "c-DC" offset," and "floating charged-DC offset."

In various embodiments, a fully rectified waveform (e.g., sinusoid, square wave, or other) may be applied to an area of tissue. The terms "full wave rectified waveform" or "fully rectified waveform" are used interchangeably herein to refer to a waveform in which both polarities of an input signal are converted to a single polarity or to substantially a single polarity. That is, the voltage of the waveform maintains a substantially single polarity, and therefore has a non-zero average voltage. Modeling tissue as a circuit, applying a fully rectified waveform results in the conservative circuit elements accumulating and storing charge (i.e., capacitance). Since this waveform maintains a single polarity and is not forcibly returned to a baseline voltage, it is never discharged, and develops a voltage offset (i.e., a DC-offset). Accordingly, within a number of cycles of the applied fully rectified waveform (e.g., 2-3 cycles using a controlled voltage), a current flow is developed through the tissues. Specifically, the developed DC offset generates a transmembrane voltage gradient in the tissue, which causes current flow to occur and it is not the same current that is being applied by the equipment.

Based on testing by the inventors, it is believed that through the application of a floating charged-DC offset to neuronal cell membranes, a transmembrane voltage gradient results leading to transmembrane macro-current flow. The DC offset that develops generates a transmembrane voltage gradient in the nerve, which causes a current flow that is independent of the current being applied by the source.

This transmembrane current flow will reinforce the normal current flow through some voltage-gated channels, but oppose the normal current flow through other voltage-gated channels, due to their directionality across discrete regions of the neuronal cell membrane. Such reinforced or opposed, time-variant current flows may behave a phenomenological capacitances and inductances.

The DC offset in the various embodiments may develop as a result of the electrical anisotropicity of nerve axons, and the resultant preferential intra-axonal current flow.

FIG. 1 illustrates a circuit model of tissue in which tissue-equivalent electrical circuits represent a portion of tissue that includes neuronal cell membranes of a peripheral nerve. In the tissue 100, a current source 102 may provide current flow in the direction of one of two surface electrodes 104 on the skin 106. Due to the various circuit elements of the tissue 100, the current may flow along multiple different paths to a second surface electrode 104.

In particular, as shown by arrow 108, the current may flow from the first surface electrode 104 to a transverse subcutaneous tissue path represented by parallel RC circuits 110, and to a longitudinal subcutaneous tissue electrical equivalent circuit. In various embroilments, the equivalent circuit may represent a path through surrounding non-nerve tissue 112 to another surface electrode 104.

As shown by arrows 114 and 116, the current flow may unevenly divide between the path through the surrounding non-nerve tissue 112 (i.e., extraneuronal path), and a path across the nerve cell membrane 118 and down the axoplasma of the nerve cell interior 120 (i.e., neuronal tissue path). In some embodiments, the series resistance of the neuronal tissue path may be 250 Ohms, while the effective series resistance of the extraneuronal path may be 1 kOhm. The nerve cell membrane 118 may have longitudinal resistance of, for example, 100 MOhms.

As shown by the relative sizes of arrow 114 and 116, the bulk of the current flow is along the neuronal tissue path. Such difference may be the result of a number of properties of the tissues and/or nerve cell membranes. For example, the current may tend to flow to the nerve cell interior 120 because of the resistance, phenomenological inductance, and capacitance characteristics of the neuronal cell membrane, particularly as the ion conductances of voltage-gated channels begin to change in response to the applied current. Further, once current is within the nerve cell interior 120, it may tend to remain on the axoplasmic path due to the lower impedance than the extraneuronal path. Specifically, since the axoplasma is essentially uninterrupted conduction material, it does not have any cell membrane barriers to longitudinal current flow. Therefore, the neuronal tissue path exhibits an ohmic resistance that is much lower than the impedance outside the nerve cell. As a result, current may continue to flow along the neuronal tissue path until it reaches the other surface electrode 104, where current flow exits and returns to the source 102.

The developed voltage across the extraneuronal path is shown to the left and the axonal path voltage is shown below the electrical circuit diagram. Since the magnitude of the longitudinal series resistance of the membrane is very much greater than either the extraneuronal series resistance or the axonal series resistance, longitudinal intramembrane current flow is negligible.

Because the larger amount of current flowing into and inside the nerve than outside the nerve, in various embodiments a voltage difference may develop between the extraneuronal path and the neuronal tissue (i.e., axonal) path for current. Specifically, different voltage traces may be observed inside the nerve and outside the nerve in response to the applied current. These differences in voltage may result, for example, from the difference in resistivities that lead to the preferential current flow in the neuronal tissue path (i.e., ohmic resistance inside the nerve, and impedance outside the nerve).

Figure 2A:
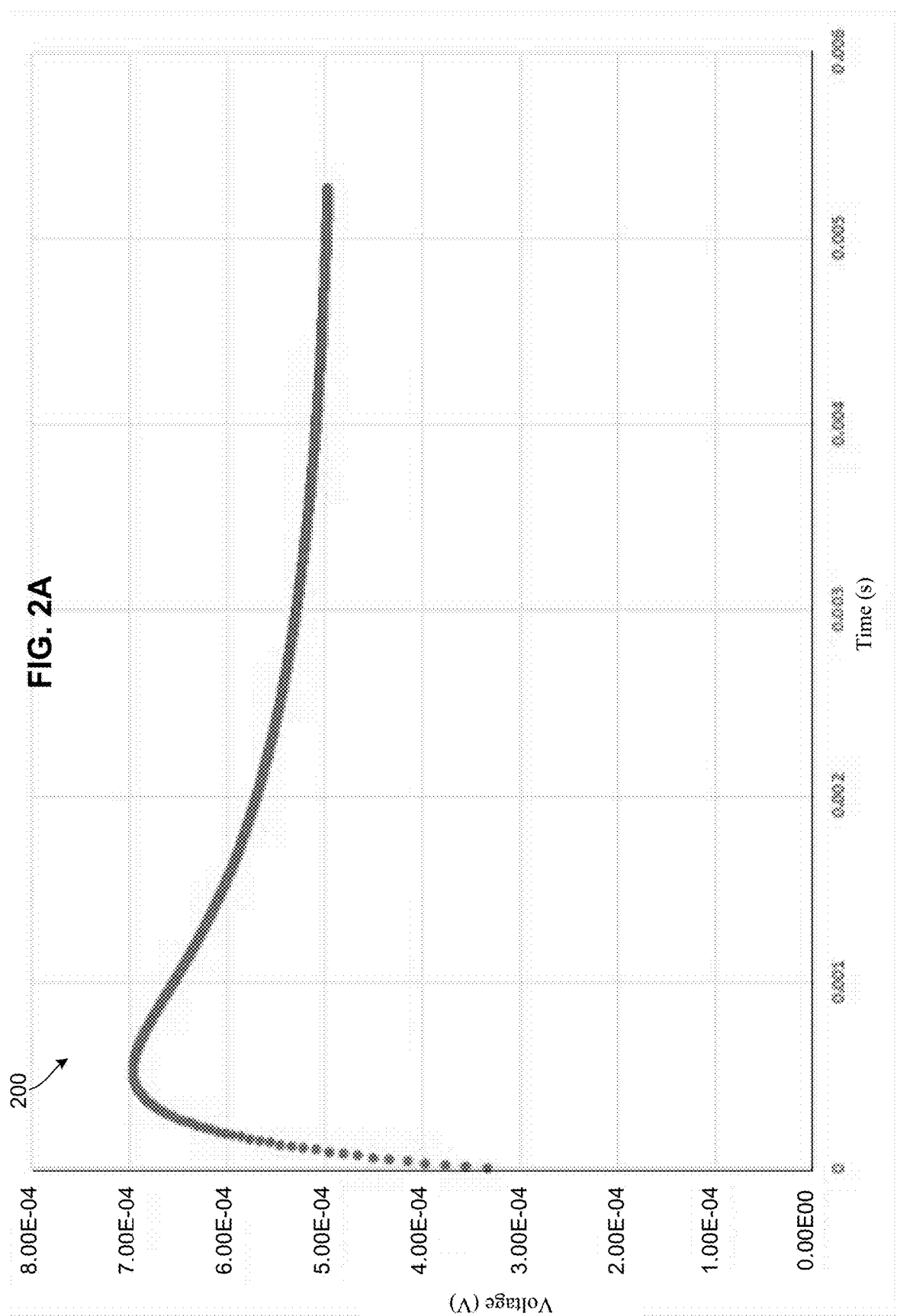
FIG. 2A is a plot illustrating a voltage developed in the extraneuronal tissue path of FIG. 1 as a function of time during application of a current pulse.
Figure 2B:
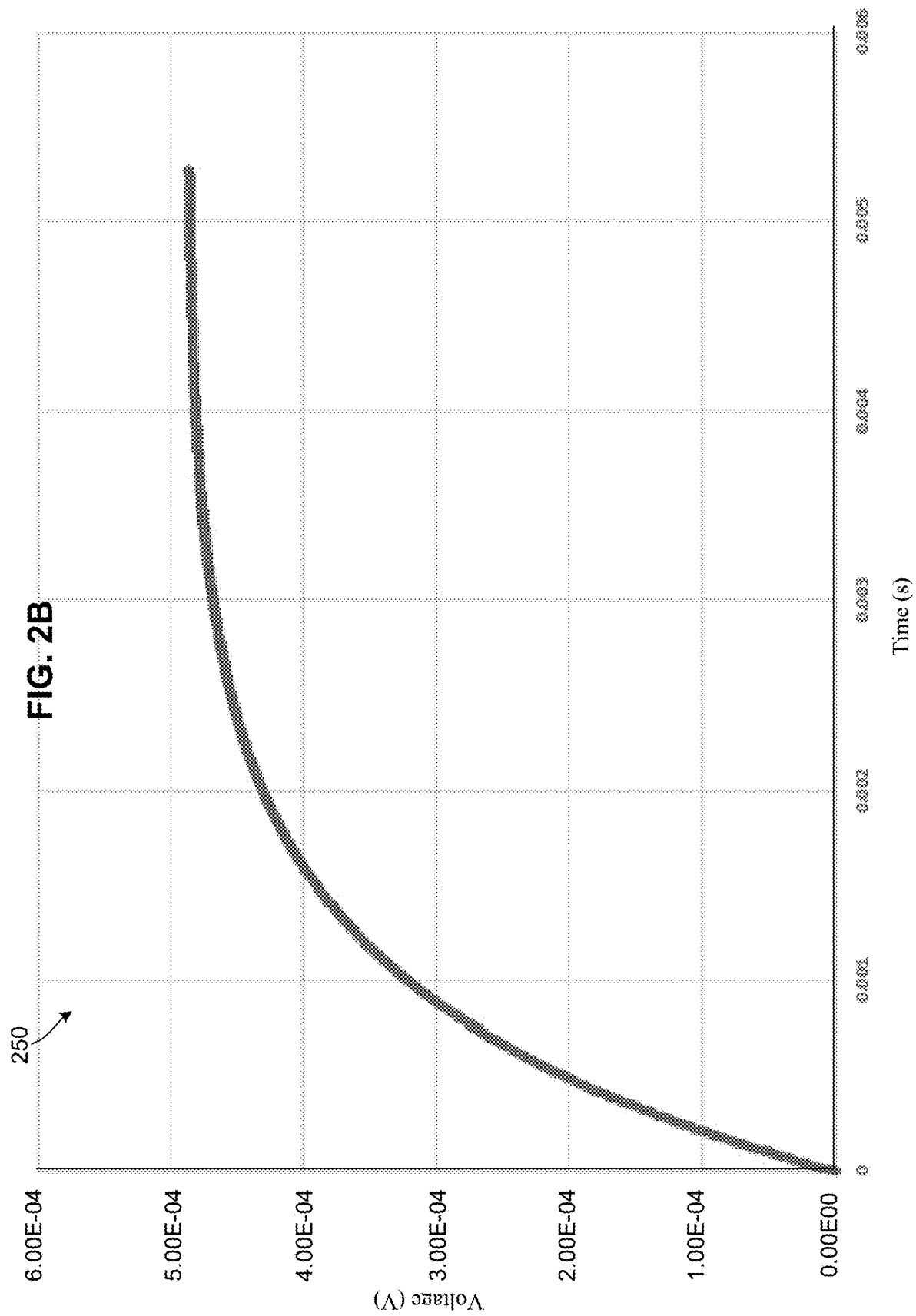
FIG. 2B is a plot illustrating a voltage developed in the neuronal tissue path of FIG. 1 as a function of time during application of a current pulse.

Examples of these voltage traces are shown in FIGS. 2A and 2B. With reference to FIGS. 1-2B, the voltage curves 200 and 250 may be derived using the representative parameters of the tissue 100.

In particular, FIG. 2A shows the voltage that developed in the axoplasma (i.e., the nerve cell interior 120) over the cycle of an applied 200 Hz pulse. FIG. 2B shows the voltage that developed outside of the nerve cell (i.e., the non-nerve tissue 112) over the same applied 200 Hz pulse.

The voltage curves 200 and 250 show a phase difference or lag (i.e., difference in the waveform positions of the voltages inside and outside the neuronal cell membrane). As shown, the voltages that develop in the extraneuronal path (i.e., voltage curve 250) peak much earlier than the voltages developed in the axonal tissue path (i.e., voltage peaks) on a given pulse.

Without wishing to be bound by a particular theory, such phase difference may be a characteristic that enables the DC offset to develop, and therefore enables the voltage gradient that drives current across the membrane. Specifically, as a result of the differences between the voltages developed in the extraneuronal and axonal tissue paths, a net current will flow from outside the nerve cell to the axonal path during the initial portion of the applied current pulse (i.e., 200 Hz). Over the duration of the pulse, the voltage gradient changes so that the net current will flow in the opposite direction as the voltage develops in the axonal circuit.

Figure 2C:
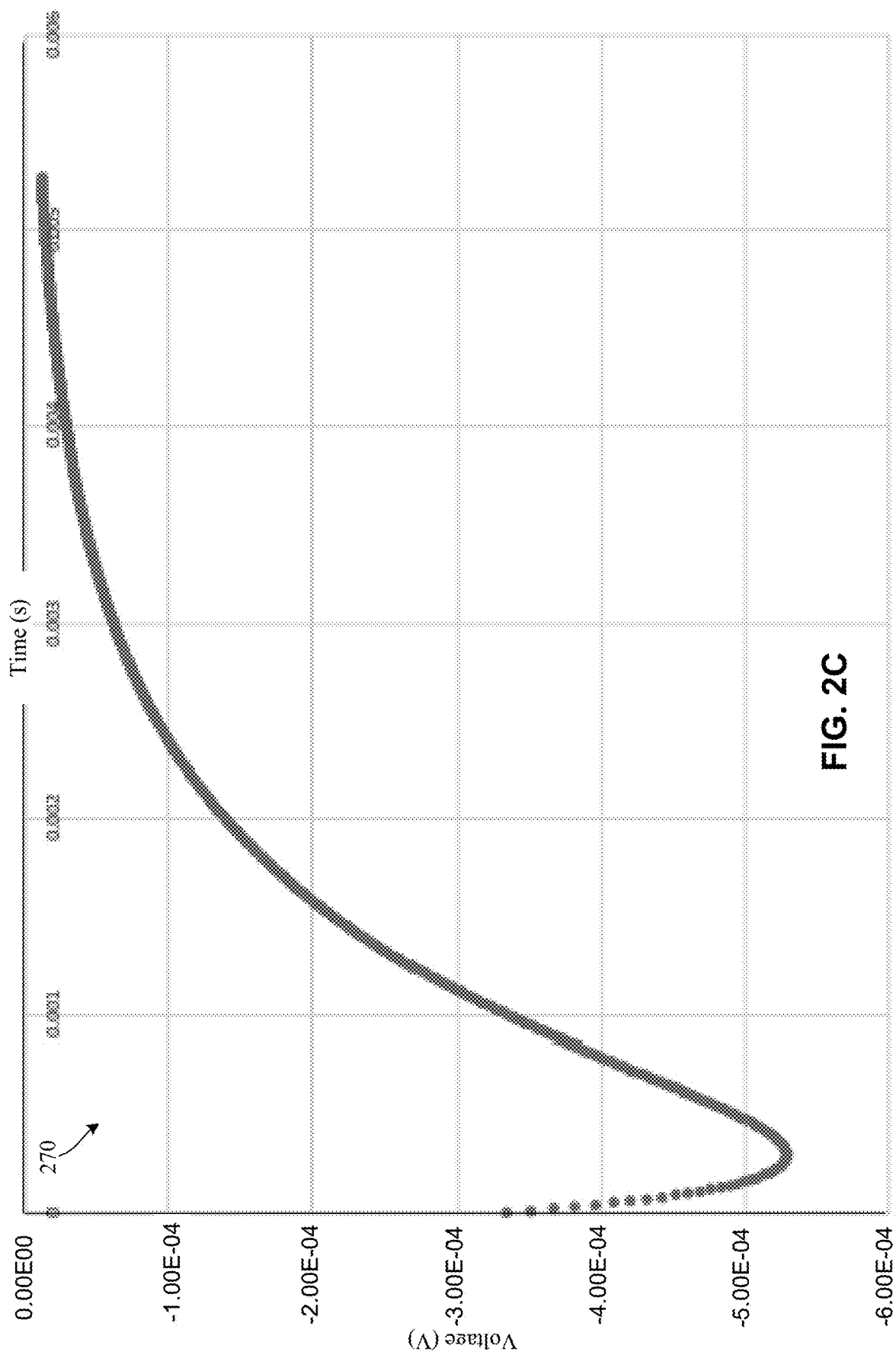
FIG. 2C is a plot illustrating the voltage differences between the extraneuronal and axonal tissue paths of FIG. 1 during application of a current pulse.

FIG. 2C shows the differences between the developed axonal tissue path and extraneuronal tissue path voltages over the time of the applied pulse. Referring to FIGS. 1-2C, a voltage differential curve 270 may be created by subtracting the values of the voltage curve 250 from those of the voltage curve 200, and plotting the differences against the same single current pulse duration used in FIGS. 2A and 2B.

As shown by the dip 272 in the voltage differential curve 270, the voltage gradient may initially cause the transmembrane current to flow from outside the nerve cell to the axonal tissue path. As the pulse continues, the voltage gradient may cross a threshold in which it causes the transmembrane current flow to switch from the nerve cell interior to the extraneuronal tissue path.

The lowest point 272 of the voltage differential curve 270 may correspond to a current pulse at around 3 kHz (i.e., around 0.33 ms). Therefore, the transmembrane current flow may be maintained in the direction of outside to inside the nerve cell by applying the current pulse at a frequency of around 3 kHz or more. That is, a waveform having a high frequency may be used in various embodiments to ensure a unidirectional (i.e., outside to inside the nerve cell) current flow across the neuronal membrane. Depending on the magnitudes of the series resistances in the extraneuronal and axonal circuits, the lowest point 272 of the voltage differential curve 270 may shift in time, and that time and corresponding frequency of 0.33 ms are only provided herein as examples. Further, the voltage gradient may be significantly affected by change in the current dependent, time-variant ionic conductances of the neuronal membrane (e.g., shown as series batteries and resistances in neuronal membrane 118). For example, such ionic conductances may initially be very high, but may rapidly fall with the application of an external current, further increasing intra-axonal current flow.

When a time-variant waveform is superimposed on the transmembrane current flow, the time-variant resistances of the voltage-gated channels causes the channels to behave as phenomenological capacitive and inductive reactances. The presence of both kinds of electrical reactance provides for electrical resonance at a resonant or critical frequency of the applied time-variant electrical waveform.

To enable electrical resonance in tissue elements that are current dependent, time variant resistances (e.g., the conductances of the voltage-gated channels in the neuronal membrane 118), a continuous current flow across the membrane, which is modulated in time, may be maintained.

In various embodiments, a continuous current flow is maintained by employing fully rectified waveform that does not cross the zero volts line (at least on average). That is, since the waveform never returns to baseline, the conservative tissue elements (e.g., membrane capacitances) are kept charged. The resulting DC-offset, voltage gradient results in a continuous transmembrane current flow. Further, since the continuous transmembrane current flow is modulated by the difference in phase angle between the peak voltage values developed in the extraneuronal path (i.e., voltage curve 200) and in the axonal path (i.e., voltage curve 250), the continuous transmembrane current flow is modulated in time.

Various embodiment methods and devices leverage the effects and benefits of inducing resonant behavior of neurons and/or continuous transmembrane current flow for a number of medically beneficial applications. Many medically beneficial applications are contemplated, including without limitation nerve blocks and electrically induced analgesia pain management systems, transcutaneous neuromodulation, neuromodulation device battery life extension, neuromodulation device fibrous tissue accommodation, enhanced TENS enkephalin release, enhanced spinal cord stimulation, enhanced deep brain stimulation, enhanced peripheral nerve stimulation, three-dimensional impedance neurography, local anesthetic onset/offset detection, and smart prosthetics. Without intending to limit inventions and applications, descriptions of application embodiments begin with descriptions of analgesic applications.

Inducing resonant behavior of neurons results in electrical oscillation of the neuronal cell membranes and blockade of action potential propagation. Specifically, at a resonant frequency, impedance peaks in a parallel RC circuit correspond with minimal or no ion conductance through the voltage-gated channels blockage of action potential formation and propagation. By applying a time-variant waveform with a floating charged-DC offset, transmembrane time-variant current flow occurs, causing electrical oscillatory behavior of the neuronal cell membrane at the critical frequency and blocking of action potential propagation along axons.

Utilizing electrical fields to generate physiological responses in nerves has been seen in several areas of research, including sleep, movement disorders, and analgesia. Electrical nerve stimulation to induce analgesia has numerous advantages over other anesthetic techniques. There is little potential for overdose, physiological addiction, and other adverse effects. In addition, this method provides anesthetic effects rapidly after placement, and these effects go away quickly after cessation of application.

These features may be valuable for post-surgical pain relief, particularly in Cesarean section cases. Decreased use of pain medication limits the incidence of passage of medication into breast milk and thus reduces the likelihood of adverse effects of medication on the breastfed infant. In addition, electrodes may be conveniently placed to align with subcostal and iliohypogastric nerves after labor to minimize nociception in the localized abdominal region.

Several previous patents have addressed the use of electrical nerve stimulation through resonance and a DC offset for various pathologies and pain relief Most notably, U.S. Pat. No. 5,782,874 discusses a method for inducing resonance in neural circuits by application of weak electric fields by proximal electrodes. Subsequent patents by Hendricus G. Loos discuss modulation of electrical spikes in afferent nerves (U.S. Pat. No. 6,167,304). In addition, several patents, including U.S. Pat. No. 4,924,880 for a dental anesthesia apparatus and U.S. Pat. No. 5,117,826 for biphasic pulse stimulation, address the need for a DC offset to enhance antinociception. However, these patents refer to a physiologic resonance, but do not describe the electrical waveform application necessary to produce electrical resonance. In addition, the patents that utilize a DC offset do not specify the methodology for application of a DC offset. While these patents acknowledge a need for a non-zero DC charge to aid in pain relief, they do not indicate that this DC charge must be generated over the entire electrical path from cathode to anode, rather than being merely an applied offset voltage.

Notably, the presence of multiple resonant peaks indicates that this technique may be used to target specific neuronal fibers. Depending on the resonant peak selected, action potentials of particular groups of fibers may be blocked, resulting in different physiological responses. For example, selecting a resonant frequency for cell membranes of groups of motor neurons may produce muscle weakness. Alternatively, groups of A-delta or C fibers may be blocked, limiting sharp or dull pains. This fine adjustment of resonance allows the methods and devices of various embodiments to be used for various needs and impairments that may be tailored to an individual patient.

Various acute and/or chronic pain management systems may be developed as electrical resonance-induced analgesia/anesthesia. Such pain management systems may be based on the techniques discussed herein for provoking parallel electrical resonance of nerve cell membranes using skin surface electrodes. In this manner, a non-invasive and non-medication-based pain relief system is enabled. Specifically, transcutaneous application of subthreshold time-variant waveforms may provoke neuronal cell membrane electrical resonance. Electrical impedance of the nerve membrane may be maximized at a critical frequency, indicating that ionic conductance (e.g., ion movement through voltage-gated sodium and potassium channels) is minimized, and therefore that action potential propagation is interrupted. In this manner, high quality analgesia or anesthesia may be provided using a skin surface electrode system.

Electrical resonance-induced pain management in the various embodiments may eliminate side effects and systemic toxicity related to medication use, and may be non-invasive as opposed to implanted electrostimulation devices, such as spinal cord stimulators. Further, such pain management systems are not limited to low level pain intensity situations where transcutaneous electrical nerve stimulation (TENS) therapy or behavioral cognitive therapies are employed with variable success.

The systems may be configured to automatically identify the position of a nerve of importance, such as using impedance neurography techniques or resonance peak mapping, discussed in further detail below. Additionally, pain management systems according to some embodiments may be less uncomfortable to patients since the subthreshold electrical stimulation is not associated with electric shock sensation during treatment.

In various embodiments, pain management systems may include electrical circuitry capable of multiple frequency sweeping and application of an electrical signal at a single critical frequency via skin surface electrodes. The electrical circuitry may be programmed to accurately determine critical, resonant frequencies based on impedance measurements across a range of frequencies.

In various embodiments, systems may be designed to produce either a complete sensory/motor nerve blockade, or a selective motor or sensory nerve blockade. In some embodiments, individual neuronal subpopulation resonance peaks may be obtained by sweeping small frequency intervals for individual impedance peaks that are not observable using larger frequency ranges.

Selective nerve subpopulation blocking may be particularly useful in certain surgeries and/or pain management for certain conditions. For example, diabetic neuropathy does not require motor nerve blockade, but would particularly benefit from selective blocking of particular groups of sensory nerve fibers in the somatosensory system fibers (e.g., Group C nerve fibers and/or A-delta nerve fibers). Therefore, selective nerve subpopulation blockade systems in various embodiments may be used to provide diabetic neuropathy pain relief without relying on drugs, and without blocking other nerve functions (e.g., motor nerves).

In various embodiments, an electrical resonance-induced pain management system may be configured as a patch system containing an array of sampling electrodes and at least one return electrode. In some embodiments, the patch system may be "smart patch" that is configured to automatically locate a target nerve using impedance neurography, and select the appropriate sampling electrode(s) in order to scan to determine a critical frequency for electrical resonance of the neuronal cell membranes. In smart patch systems that are configured to perform automatic nerve detection based on impedance neurography, one or more return electrode may be included and configured to be positioned at a pre-determined minimum distance from the sampling electrode(s), such as 15-20 cm.

Specifically, an embodiment smart patch system applied to the skin may be configured to measure impedance across a plurality of sensing electrodes in an array, thereby mapping a location of the nerve of interest for pain management. Based on the location of the nerve, the smart patch system may select one or more electrodes correctly positioned in proximity to the nerve, for use in detecting an electrical resonant frequency. That is, the smart patch system may be configured to apply signals at varying frequencies between the selected sampling electrode(s) and one or more return electrode until a frequency at which electrical resonance occurs is detected. In various embodiments, the application of signals at varying frequencies to identify resonance may involve quickly sweeping a fairly broad range of frequencies at large incremental steps, which may be subsequently narrowed. For example, the smart patch system may sweep a first range of frequencies that is inside the outside bounds of 0 and 20 kHz, such as 1-10 kHz, 2-6 kHz, etc., at 200-Hz steps. If the resulting impedance measurements begin to indicate resonance at a particular frequency step, a more refined sweep may be done of the frequency range for that 200-Hz step. For example, the smart patch system may sweep the range of frequencies at 10-Hz steps. Such repetition using further refined frequency sweeps may be repeated any number of times at progressively narrower ranges, depending on the programming of the smart patch system.

Once the critical frequency is determined, an electrical signal may be applied to the selected electrode(s) at that critical frequency. For example, a subthreshold, fully rectified waveform of the critical frequency may be applied to the skin via the one or more electrodes.

In another pain management system embodiment, the location of the nerve may be determined by landmarking anatomy as opposed to automatic mapping based on impedance neurography techniques. Depending on the nature of the pain relief sought and the target nerve and can identify the location of target nerve, such systems may be suited for use by medical and/or other professionals having specialized knowledge in anatomy. For example, a patient who has just undergone a Cesarean section may use the patch system as a desirable pain relief tool instead of medication (e.g., opioids). A doctor may easily identify the location of a target nerve, and therefore the placement of the electrode(s), relative to the incision from the Cesarean.

A wide range of pain relief, anesthesia, and/or other nerve block applications may benefit from the systems and techniques of the various embodiments.

In some systems, a smart patch or other pain management patch system described herein may be designed for use as an alternative to over-the-counter pain relievers. Such system may be disposable and/or temporary in some embodiments. Alternatively, the system may be reusable in some embodiments. In some embodiments, various pain management patch systems may be applied by a patient or consumer, and may be configured to run until removed by the patient or consumer.

In some embodiments, pain management systems may be simplified and implemented on a single patch by using resonance peaks for the automatic mapping functionality to identify nerves of interest rather than impedance neurography. Specifically, a controller of the single patch system may be configured with an algorithm that searches for a maximum magnitude resonant peak at the lowest frequency. When a nerve lies normal to the complex curve of the skin surface, resonance-related impedance is maximized and appears to occur at the lowest frequency. Lateral to that position, resonance peaks may be present but of lesser magnitude and are displaced to higher frequencies. This resonant peak magnitude relationship to skin position may enable the pain management system to be a single patch in which the return electrode(s) is included in the same array as, or at least within close proximity to, the sampling electrodes of the array. That is, the distance separation between the sampling and return electrodes is not as critical for resonance peak detection as it is for impedance neurography. Further, this single patch system may enable a number of different electrode configurations for sampling and return electrodes, providing significant flexibility in how the patch and array are structured.

The single patch pain management system may operate by performing a frequency sweep on each sampling electrode in order to identify resonance frequencies, as well as their corresponding magnitudes.

Some embodiments include a method for electrically inducing resonance of the nerve fibers. Such embodiments may utilize rapid waveform transmission to generate electrical resonance of nerves. Time-variant waveforms of this frequency may be then sent through nerve fibers with a charged-DC offset to block neuronal depolarization, yielding an analgesic effect. This analgesic effect may be amplified by construction of low frequency electrical stimulation from high frequency waveform components to create both a peripheral nerve blockade and enkephalinergic inhibition of ascending neuronal transmission. By constructing a low-frequency pulse from high frequency components, the neuronal cell membrane is subjected to a net, non-zero root mean square (RMS) voltage. While this low-frequency pulse is in effect, the high frequency membrane oscillations are not seen due to the RMS voltage duration of the constructed pulse being less than the resonant frequency. Propagated action potential generation is possible during this period when membrane oscillatory effects are not occurring, allowing a low frequency waveform to be transmitted to the central nervous system resulting in enkephalinergic inhibitory action of central interneurons. Alternatively, the same effect could be caused by terminating the resonant frequency time-variant waveform and constructing a DC pulse of the desired low frequency, and then resuming the resonant, high frequency, time-variant waveform until the next low frequency pulse occurs.

It is recognized that prolonged periods of continuous application uni-directional current flow may promote tissue damage. Specifically, as a result of such continuous application, charged ions may accumulate in the vicinity of an electrode (e.g., hydroxyl and chloride ions near the anode), which may cause pH changes. Therefore, to manage such potential damage, the polarity of the current may be reversed, or the device turned off, for a brief period on a regular basis in various embodiments.

Further embodiments may include the application of the floating charged-DC offset, time-variant waveform, resulting in altering the resting membrane potential of the neurons due to the resultant net transmembrane current flow. If the alteration of the resting potential results in a reduction of the electrochemical transmembrane voltage gradient, action potential generation will be possible at reduced electrical field strengths in the vicinity of the neurons. For example, when the charging waveform has a sufficiently high frequency to keep the transmembrane current flowing from outside to inside the nerve, the externally applied voltage required for depolarization and action potential formation may be reduced. That is, a 6-7 mV depolarization across the neuronal cell membrane is typically required in the resting state to cause action potential formation (i.e., to raise the membrane potential to above the threshold of around −55 mV). However, the sustained charging DC offset discussed herein may result in a subthreshold baseline depolarization of 1-2 mV, changing the membrane potential from −70 mV to around −68 mV (i.e., reducing the transmembrane voltage gradient). Consequently, less power/electrical field strength may be required of a stimulating pulse to effect action potential generation. Likewise, if the electrochemical transmembrane gradient is increased, action potential generation will require higher electrical field strengths.

Various embodiment systems may rely on a shift in membrane potentials of neuronal cells based on the DC voltage offset discussed above. In particular, embodiment devices and systems may operate by reducing the transmembrane voltage gradient (i.e., causing a less electronegative membrane potential) at a nerve of interest. For example, in some embodiments, the battery life of an implantable pulse generator (IPG), such as for a pacemaker or deep brain stimulator, may be improved.

Using a subthreshold, fully rectified waveform, a DC voltage offset may develop across the neuronal membranes. As a result of the differences between the voltages in the extraneuronal and axonal tissue paths that develop from the applied waveform, a transmembrane voltage gradient may be generated. As described above, in order to ensure that the direction of the transmembrane current driven by the voltage gradient remains from outside to inside the nerve cell, the applied waveform may have a high frequency (e.g., 2-3 kHz). As a result, the voltage step to actual depolarization of the nerve cell may be decreased, thereby lowering the amount of current required from the battery of the implanted device for depolarization. That is, a shift in the transmembrane potential resulting from the DC offset at high frequency will decrease the transmembrane voltage gradient, reducing the voltage gradient required to trigger an action potential. In various embodiments, depending on the IPG and battery specifications, the battery life may be significantly lengthened by employing this technique.

In some embodiments, shifting the transmembrane potential in a manner similar to the IPG devices (i.e., less electronegative) may be employed to lower the required power level for TENS devices.

Figure 3:
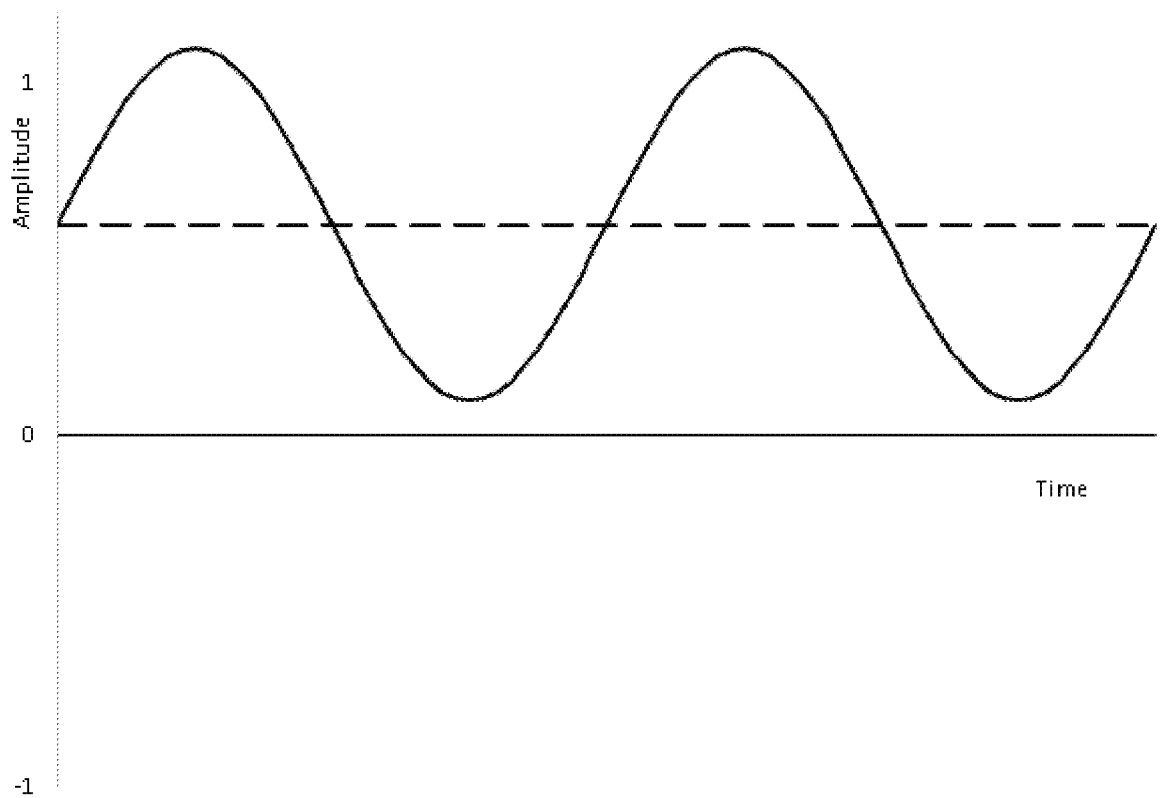
FIG. 3 is a plot illustrating a waveform with a non-zero, DC offset used in transcutaneous electrical nerve stimulation according to various embodiments.

In some embodiments, shifting the transmembrane potential in a manner similar to the IPG devices (i.e., less electronegative) may be used to improve IPG fibrous tissue accommodation. Specifically, fibrous scar tissue typically develops around the electrodes in an implanted device (e.g., a pacemaker, deep brain stimulator, etc.). As a result, the amount of power required to drive the nerves that are separated from the electrodes by such scar tissue is increased (loss of capture). By reducing the transmembrane voltage gradient, and therefore lowering the voltage requirement for depolarization, accommodating to the fibrous tissue formation on implanted devices may be improved. As a result, a patient may eliminate the need for electrode replacement FIG. 3 illustrates an example of a fully-rectified waveform created between the anode and cathode electrodes.

Figure 4:
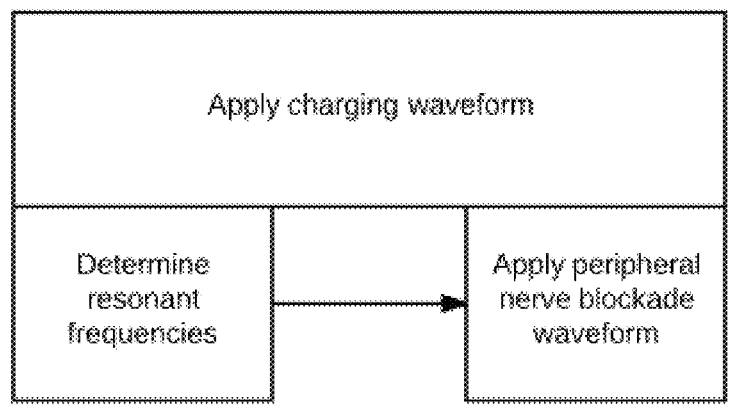
FIG. 4 is a plot illustrating the simultaneous waveform application to generate a peripheral nerve blockade according to various embodiments.

Referring to FIG. 4, while the charging waveform is applied to the nerve, resonant frequencies may be determined. For example, a time-variant waveform may be applied over a range of frequencies, with impedance measurements taken throughout the range. A resonant frequency may be identified as the frequency at which peak impedance occurs. After the resonant frequency is determined and the charging waveform is simultaneously being applied, the resonant frequency may be used to generate a peripheral nerve conduction blockade.

Figure 5:
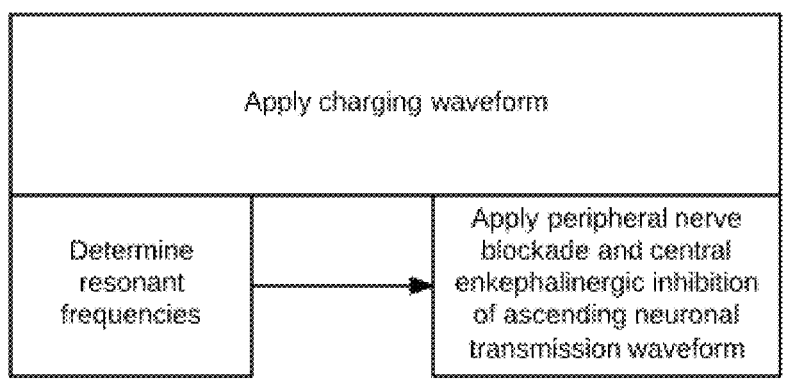
FIG. 5 is a plot illustrating the simultaneous waveform application to generate a peripheral nerve blockade and inhibition of ascending neuronal transmission according to various embodiments.

Referring to FIG. 5, while the charging waveform is applied to the nerve, resonant frequencies may be determined. For example, a time-variant waveform may be applied over a range of frequencies, with impedance measurements taken throughout the range. The resonant frequencies may be identified as the frequencies at which peak impedance occurs. After the resonant frequency is determined and the charging waveform is simultaneously being applied, the resonant frequencies may be used to generate a peripheral nerve conduction blockade. Low frequency, supra-threshold waveforms that are ideally less than 100 Hz, may be constructed from these resonant frequencies to generate central enkephalin release to inhibit ascending neuronal transmission.

Figure 6:
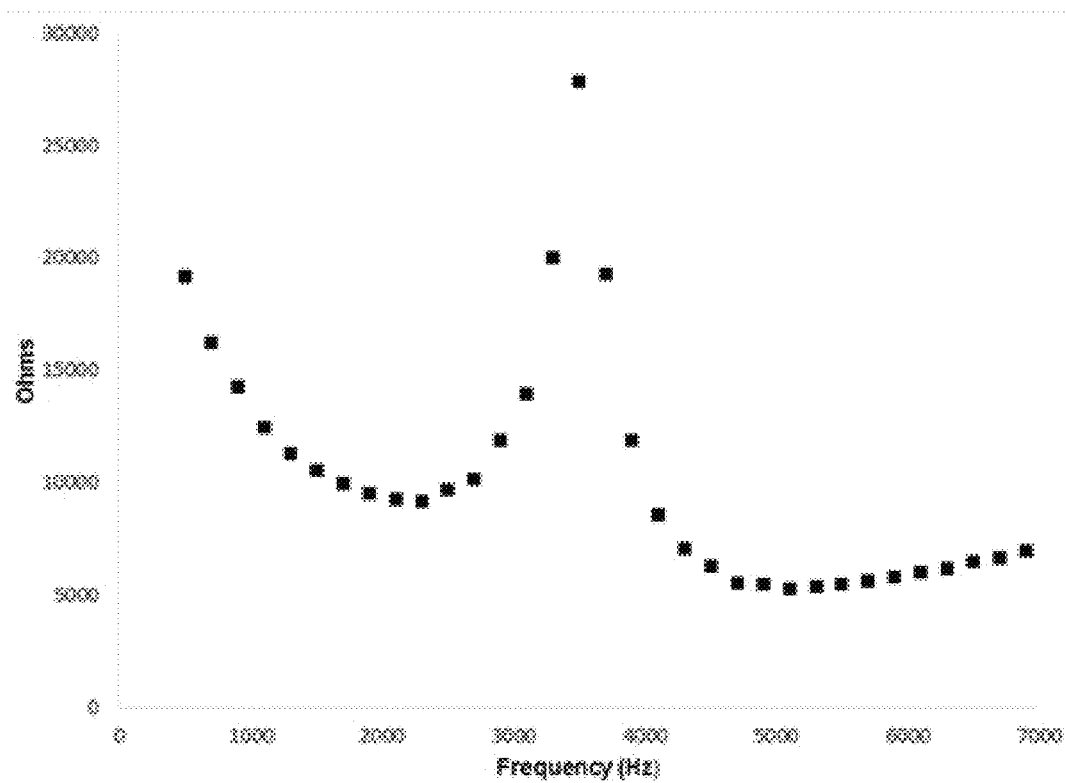
FIG. 6 is a plot illustrating the peak impedance phenomenon that may be used to determine nerve resonant frequency according to various embodiments.

FIG. 6 is a graph of resistance versus frequency of the applied wave form during testing on tissue that shows how the impedance of a nerve approaches a maximum at a frequency at which resonance of the nerve occurs. In this testing, impedance versus frequency was measured over the saphenous nerve from 500 Hz to 7,000 Hz.

Figure 7:
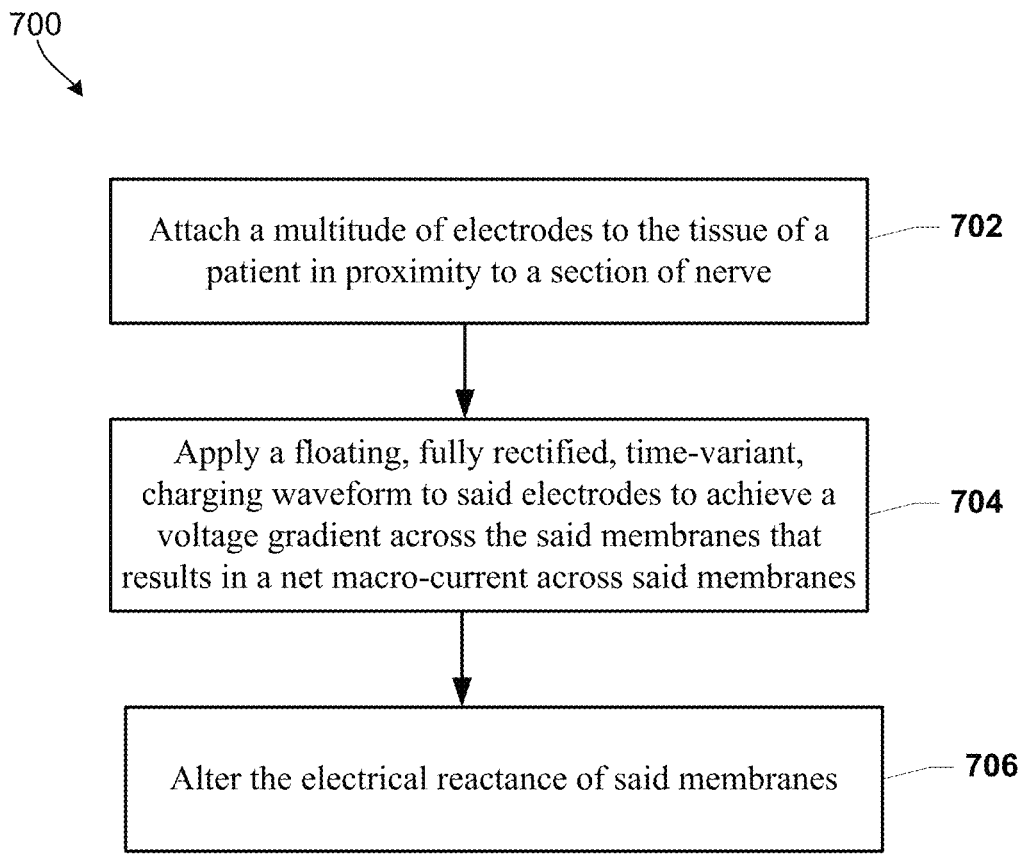
FIG. 7 is a process flow diagram illustrating a method for maintaining a net macro-current across target neuronal cell membranes according to various embodiments.

FIG. 7 illustrates a method 700 for maintaining a net macro-current across target neuronal cell membranes using an apparatus according to some embodiments. In block 702, a multitude of electrodes are attached to the tissue of a patient in proximity to a section of nerve. In block 704, a processor of the apparatus may control a power supply to apply a floating, preferably fully-rectified, time-variant, charging waveform to the electrodes to achieve a voltage gradient across the membranes that results in a net macro-current across the membranes. While it is recognized that multiple current or voltage waveforms will result in the development of a charged-DC offset resulting in a net macro-current, a fully-rectified waveform is preferred. In block 706, the electrical reactance of the membranes may be altered by the generated voltage gradient.

Figure 8:
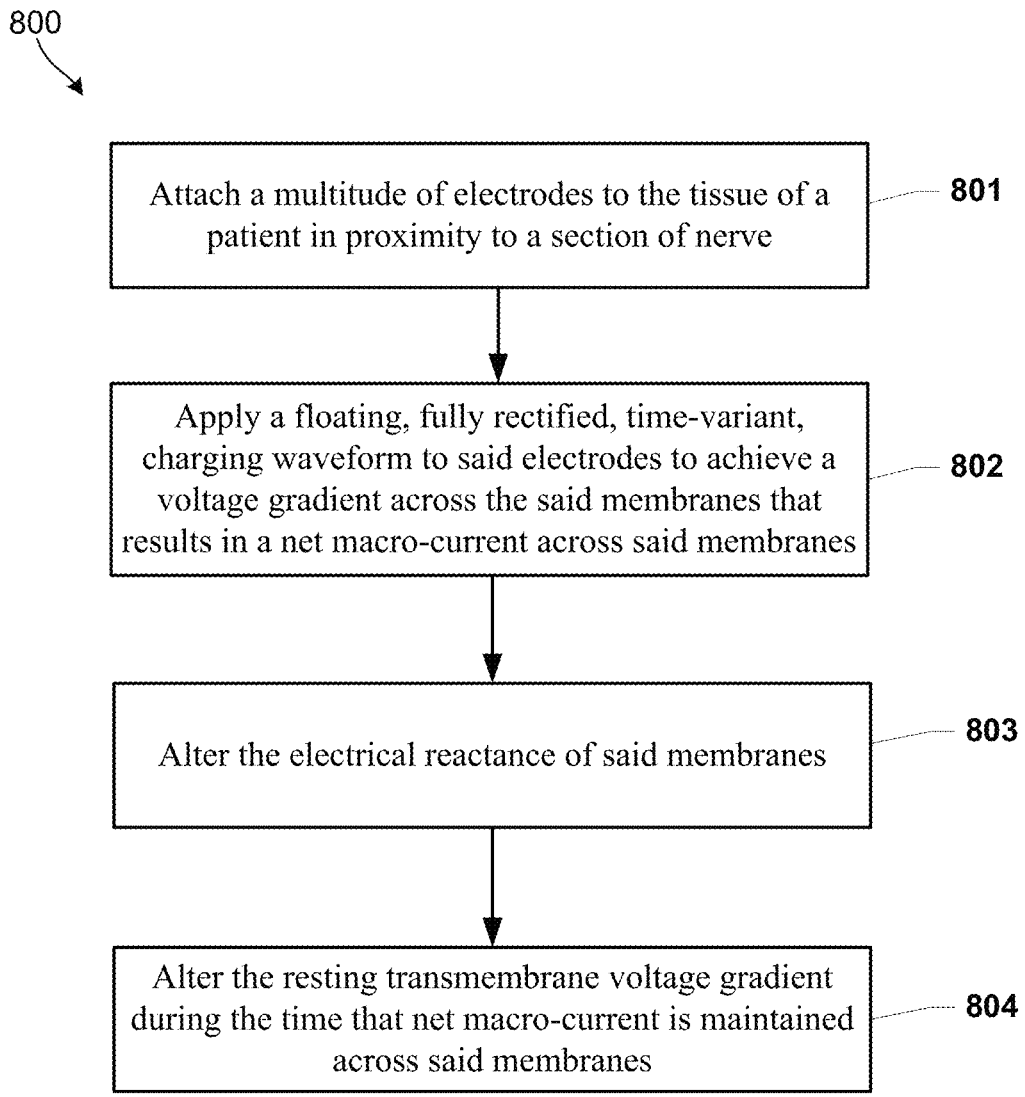
FIG. 8 is a process flow diagram illustrating a method for altering the transmembrane voltage gradient of target neuron according to various embodiments.

FIG. 8 illustrates a method 800 for altering the transmembrane voltage gradient of target neurons using an apparatus according to some embodiments. In block 801, a multitude of electrodes are attached to the tissue of a patient in proximity to a section of nerve. In block 802, a processor of the apparatus may control a power supply to apply a floating, preferably fully-rectified, time-variant, charging waveform to the electrodes to achieve a voltage gradient across the membranes that results in a net macro-current across the membranes. While it is recognized that multiple current or voltage waveforms will result in the development of a charged-DC offset resulting in a net macro-current, a fully-rectified waveform is preferred. In block 803, the electrical reactance of the membranes may be altered by the generated voltage gradient. In block 804, during the time that net macro-current is maintained across the membranes, the resting transmembrane voltage gradient is altered.

Figure 9:
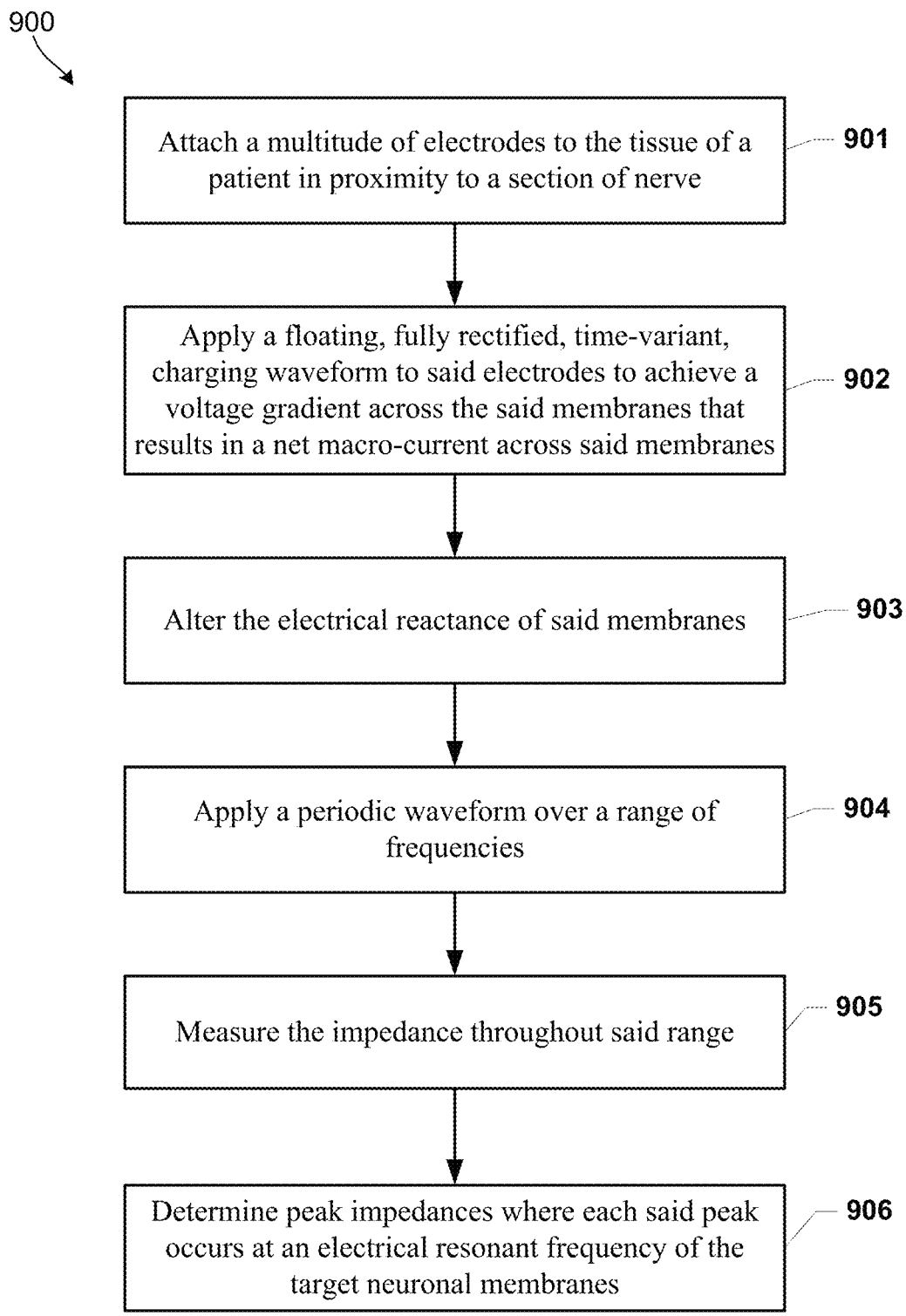
FIG. 9 is a process flow diagram illustrating a method for determining the electrical resonant frequencies of target neuronal membranes according to various embodiments.

FIG. 9 illustrates a method 900 for determining the electrical resonant frequencies of target neuronal membranes using an apparatus according to some embodiments. In block 901, a multitude of electrodes are attached to the tissue of a patient in proximity to a section of nerve. In block 902, a processor of the apparatus may control a power supply to apply a floating, preferably fully-rectified, time-variant, charging waveform to the electrodes to achieve a voltage gradient across the membranes that results in a net macro-current across the membranes. While it is recognized that multiple current or voltage waveforms will result in the development of a charged-DC offset resulting in a net macro-current, a fully-rectified waveform is preferred. In block 903, the electrical reactance of the membranes may be altered by the generated voltage gradient. In block 904, the processor may apply a periodic waveform over a range of frequencies in a frequency sweep operation. In block 905, the probes measure the impedance throughout the range of frequencies exported by the processor. In block 906, the processor may determine the peak impedances where each peak occurs at an electrical resonant frequency of the target neuronal membranes.

Figure 10:
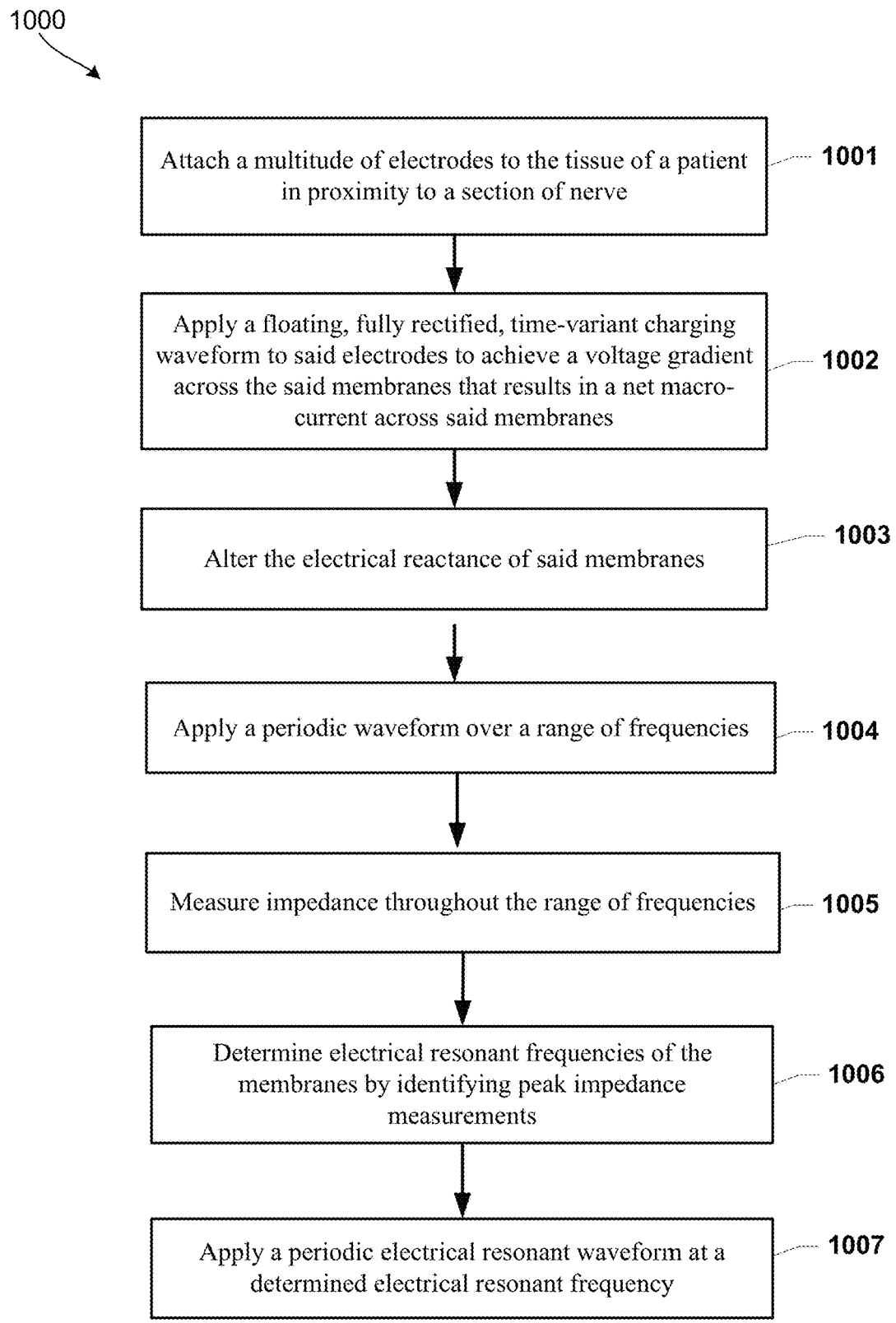
FIG. 10 is a process flow diagram illustrating a method for achieving a peripheral nerve blockade according to various embodiments.

FIG. 10 illustrates a method 1000 for achieving a peripheral nerve blockade using an apparatus according to some embodiments. In block 1001, a multitude of electrodes are attached to the tissue of a patient in proximity to a section of nerve. In block 1002, a processor of the apparatus may control a power supply to apply a floating, preferably fully-rectified, time-variant, charging waveform to the electrodes to achieve a voltage gradient across the membranes that results in a net macro-current across the membranes. While it is recognized that multiple current or voltage waveforms will result in the development of a charged-DC offset resulting in a net macro-current, a fully-rectified waveform is preferred. In block 1003, the electrical reactance of the membranes may be altered by the generated voltage gradient. In block 1004, the processor may apply a periodic waveform over a range of frequencies. In block 1005, the processor may measure impedance throughout the range of frequencies. In block 1006, the processor may determine electrical resonant frequencies of the membranes by identifying peak impedance measurements and noting the frequency at which the peak impedance was measured. In block 1007, the processor may additionally apply a periodic electrical resonant waveform at a determined frequency.

Figure 11:
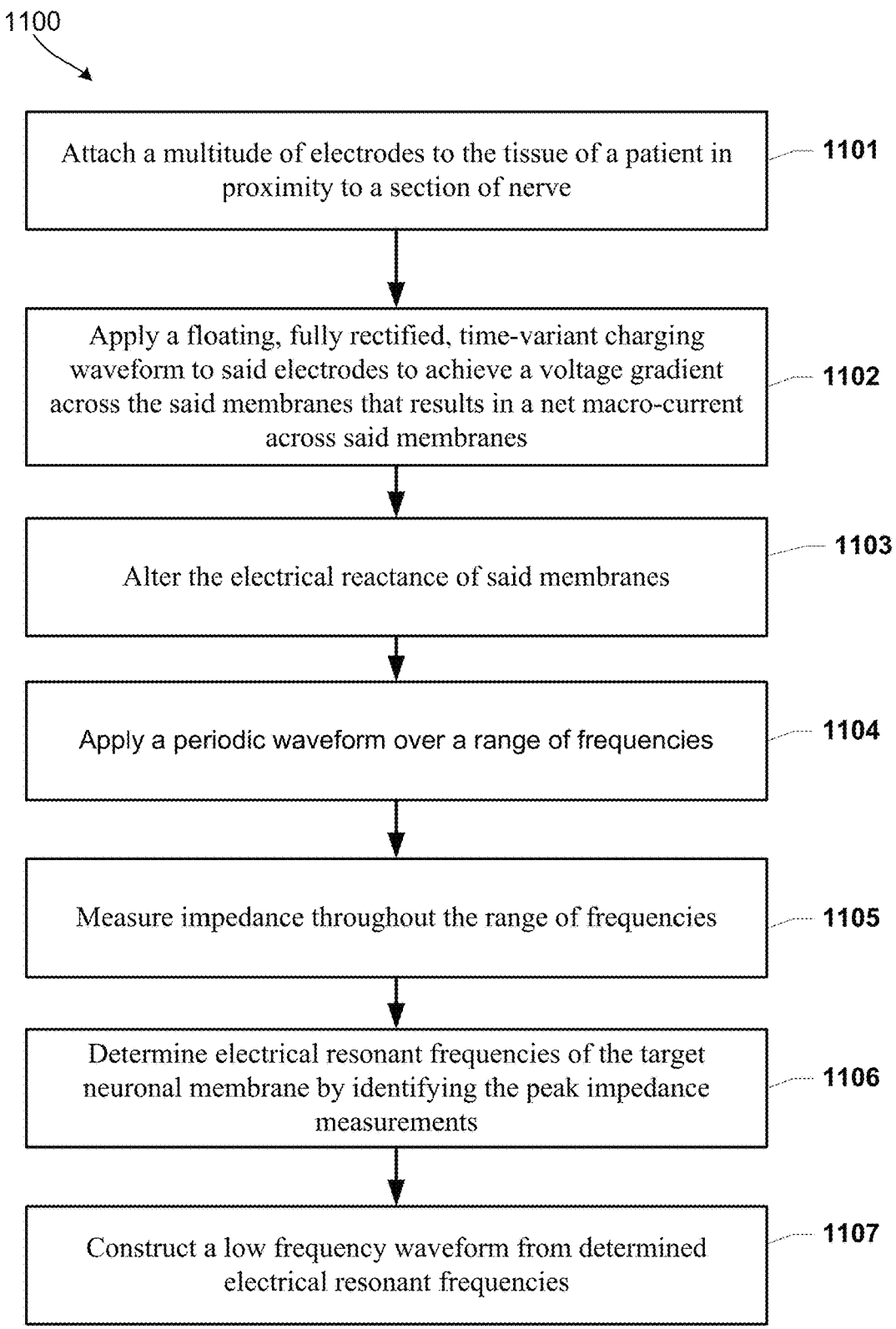
FIG. 11 is a process flow diagram illustrating a method for achieving a peripheral nerve blockade and central enkephalinergic inhibition of ascending neuronal transmission according to various embodiments.

FIG. 11 illustrates a method 1100 for achieving a peripheral nerve blockade and central enkephalinergic inhibition of ascending neuronal transmission using an apparatus according to some embodiments. In block 1101, a multitude of electrodes are attached to the tissue of a patient in proximity to a section of nerve. In block 1102, a processor of the apparatus may control a power supply to apply a floating, preferably fully-rectified, time-variant, charging waveform to the electrodes to achieve a voltage gradient across the membranes that results in a net macro-current across the membranes. While it is recognized that multiple current or voltage waveforms will result in the development of a charged-DC offset resulting in a net macro-current, a fully-rectified waveform is preferred. In block 1103, the electrical reactance of the membranes may be altered by the generated voltage gradient. In block 1104, the processor may apply a periodic waveform over a range of frequencies. In block 1105, the processor may measure impedance throughout the range of frequencies. In block 1106, the processor may determine electrical resonant frequencies of the target neuronal membrane by identifying the peak impedance measurements. In block 1107, the processor may construct the low frequency waveform from determined electrical resonant frequencies.

Figure 12:
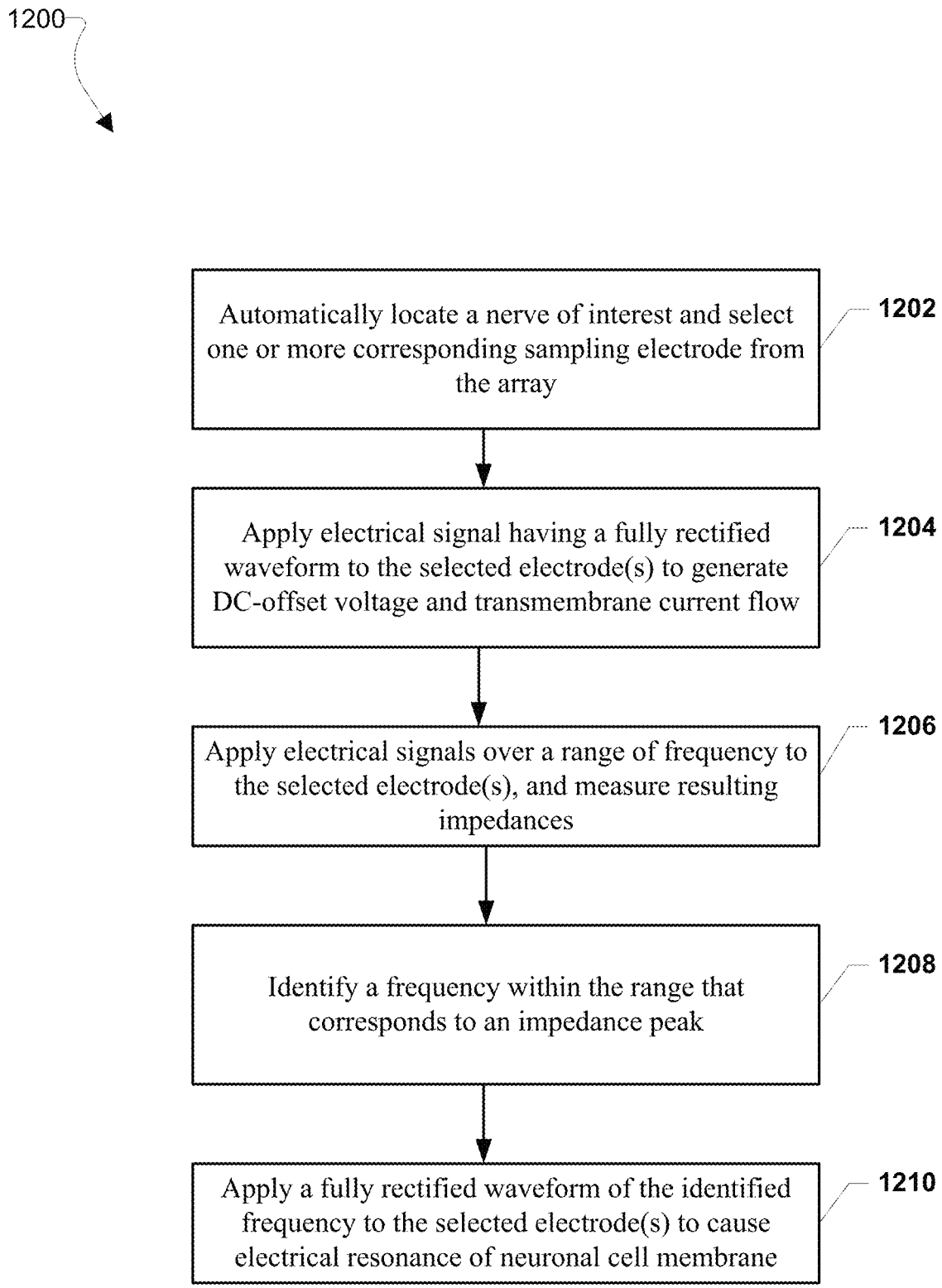
FIG. 12 is a process flow diagram illustrating a method for providing pain relief based on electrical resonance of neuronal membranes according to various embodiments.

FIG. 12 illustrates a method 1200 for managing pain by a neuromodulation electroanalgesia device. With reference to FIGS. 1-12, the operations of method 1200 may be implemented by one or more controller of any of a number of the pain management systems and/or patches described herein. In some embodiments, the neuromodulation electroanalgesia device may include an array of electrodes that can be placed on the skin in a general area of a nerve of interest.

In block 1202, the controller may automatically locate the nerve of interest and select one or more corresponding sampling electrode from the array. In some embodiments, automatically locating the nerve of interest may be performed using impedance neurography techniques, such as those describe d in further detail below. In block 1204, the controller may apply an electrical signal having a fully rectified waveform to the selected electrode(s) to generate a DC-offset voltage and transmembrane current flow. In various embodiments, application of the subthreshold fully rectified waveform may charge conservative tissue elements that have capacitances, resulting in the DC-offset voltage. The DC-offset voltage may create a voltage gradient between an extraneuronal tissue path and an axonal tissue path in the nerve of interest, thereby causing a transmembrane current flow independent of the applied waveform. As a result of the current flow and differences in voltages that develop between the extraneuronal and axonal tissue paths during the applied waveform, the current may be modulated in time, enabling resonance at critical frequencies. In block 1208, the controller may apply electrical signals over a range of frequencies to the selected electrode(s), and measure resulting impedances. In block 1208, the controller may identify a frequency within the range that corresponds to an impedance peak. In block 1210, the controller may apply the fully rectified waveform of the identified frequency to the selected one or more electrodes to cause electrical resonance of neuronal cell membranes.

Figure 13:
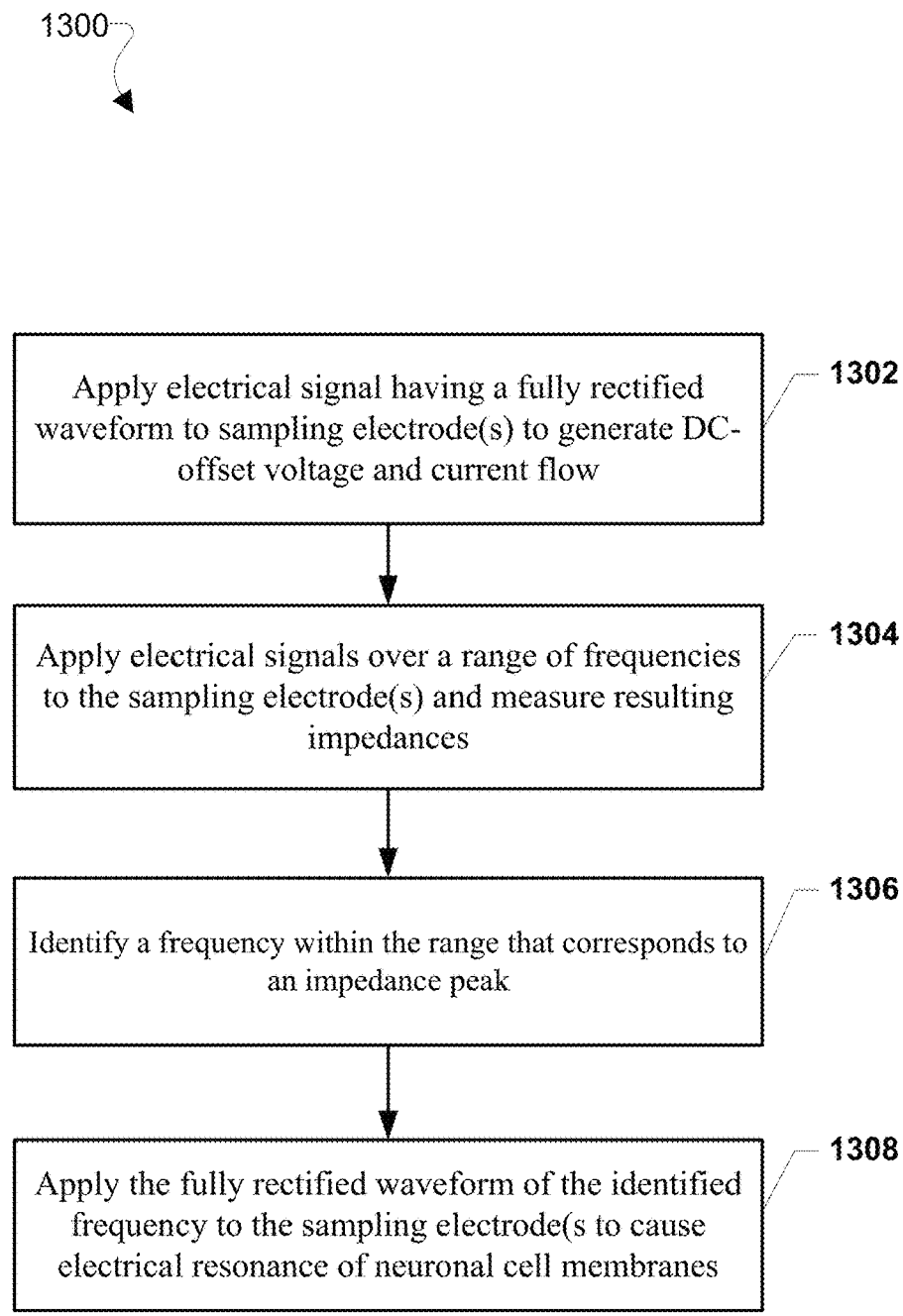
FIG. 13 is a process flow diagram illustrating a method for providing pain relief based on electrical resonance of neuronal membranes according to various embodiments.

FIG. 13 illustrates a method 1300 for managing pain by a neuromodulation electroanalgesia device. With reference to FIGS. 1-13, the operations of method 1300 may be implemented by one or more controller of any of a number of the pain management systems and/or patches described herein. In various embodiments, the neuromodulation electroanalgesia device may include a patch with at least one sampling electrode which may be applied to a skin location proximate to a nerve of interest. In some embodiments, the skin location may be identified, and the patch applied by, a medical professional or other person who can accurately identify the position of the nerve of interest. Further, the neuromodulation electroanalgesia device may include one or more return electrodes that can be placed at a skin location at a pre-determined minimum distance from at least one sampling electrode.

In block 1302, the controller may apply an electrical signal having a fully rectified waveform to the sampling electrode(s) to generate a DC-offset voltage and transmembrane current flow. In various embodiments, application of the subthreshold fully rectified waveform may charge conservative tissue elements that have capacitances, resulting in the DC-offset voltage. The DC-offset voltage may create a voltage gradient between an extraneuronal tissue path and an axonal tissue path in the nerve of interest, thereby causing a transmembrane current flow independent of the applied waveform. As a result of the current flow and differences in voltages that develop between the extraneuronal and axonal tissue paths during the applied waveform, the current made be modulated in time, enabling resonance at critical frequencies.

In block 1304, the controller may apply electrical signals over a range of frequencies to the sampling electrode(s), and measure resulting impedances. In block 1308, the controller may identify a frequency within the range that corresponds to an impedance peak. In block 1310—the controller may apply the fully rectified waveform of the identified frequency to the sampling electrode(s) to cause electrical resonance of neuronal cell membranes.

Details of impedance neurography techniques that may be used in embodiment systems and methods are disclosed in International Patent Publication No. WO2012/118751, filed Jan. 5, 2012, the contents of which are hereby incorporated by reference for the purpose of more fully describing and enabling impedance neurography techniques.

In some embodiments, impedance neurography may techniques may use electrodes of approximately 10 mm$^2$ or smaller to detect and distinguish the local variations in impedance on the skin that correspond to differences in the impedance of underlying tissue. For example, an applied signal frequency may be in the range between approximately 100 Hz and 10,000 Hz. To determine local impedance at each electrode within an array, the local effect upon the signal applied between the waveform and return electrode may be measured.

The axons that comprise a nerve, with their long stretches of cylindrical cell membrane and, in many nerves, their multiple wrappings of Schwann cell membranes (the myelin sheath), are large capacitive structures. Because the axons of a nerve represent a parallel conductor, the total capacitance is the sum of the individual axonal capacitances. Consequently, resistance within nerves may be expected to be at a minimum compared to other tissues, whereas the capacitance of nerves may be expected to be at a maximum compared to other tissues. The relatively low internal resistance and large capacitance of the axons comprising nerves, compared to other tissues, may contribute to the ability to detect nerves.

Impedance neurography may involve discriminating nerve tissue by identifying the (x, y) position of the nerve relative to a waveform electrode array, and by determining the depth position of the nerve using preferential pathways of the nerve, and impedance calculations in addition to the (x, y) determination. Further electrical characteristics and/or electrical state determinations may be used to contribute to the nerve discrimination in the various embodiments, for example, differential concentration, distribution, state (closed, inactive, or open) of voltage gated channels, as well as the geometry and electronic properties of tissues, including the geometry (i.e., linear runs and branches) and electronic properties of nerves.

It is believed that the narrow zones of low impedance exhibited on the skin directly above nerves are due to the fact that axon fibers preferentially rise from the nerve at approximately right angles to the skin surface and do not reach the skin at angles less than about 90 degrees. Thus, the low impedance zone due to the preferential conduction path through axon fibers appears just in the narrow zone of the skin that lies directly above the nerve. As such, in an embodiment, the presence and location of nerves may be revealed by localized zones (typically narrow lines) of low impedance measured on the skin. It has been found that in order to sense the local low impedance associated with an underlying nerve, the waveform electrodes may be constrained to a small area, preferably about 10 mm$^2$ or smaller.

In the controlled current mode, measurements of the sensed signal may be made immediately upon applying the source signal, after approximately 100 cycles (or more), or at any time in between, more preferably after approximately 20 cycles. A tissue charging effect is observed when using a controlled current waveform, necessitating about 50-70 cycles to complete the charging effect. The tissue charging effect is not observed using controlled voltage, since current is allowed to "float" and charging may occur within 2-5 cycles. As such, in the controlled voltage mode, measurements of the sensed signal may be made immediately upon applying the source signal, after approximately 100 cycles (or more), or at any time in between, and more preferably after approximately two to approximately five cycles.

The impedance (Z) may be determined for all the electrodes in the array. At low frequencies (e.g., less than 1500 Hz), electrodes with the lowest Z value will overlie the course of the nerve structure most directly, or have the largest quantity of nerve tissue (e.g., a nerve branch point) underlying those electrodes. In an embodiment, the resistive (R) and reactive (X) components of Z may be derived, noting that the electrodes demonstrating the lowest resistivity, or highest capacitance, will most directly overlie the course of the nerve structure. Other, derivative functions of current or voltage related to frequency, time, or distance may also be used to indicate the position of nerve structures.

In some embodiments, three-dimensional impedance neurography may be performed using the two-dimensional impedance neurography techniques herein. Specifically, depth information may be derived from the surface impedance measurements. The depth information may be combined with the two-dimensional impedance information to generate and display three-dimensional information. In various embodiments, software systems may be programmed with algorithms and instructions to automatically obtain such depth information from surface impedance measurements taken during the two-dimensional impedance neurography.

In some embodiments, impedance neurography may be used in a system to accurately detect local anesthesia onset and offset. Specifically, impedance changes in skin surface measurements have been observed in association with the starting and stopping of effects of local anesthetic agents (e.g., sodium channel blocking agents). These impedance changes, which are associated with voltage-gated channel dysfunction, occur prior to any sensory change experienced by the patient.

In continuous regional anesthesia techniques, catheters connected to a pump to infuse local anesthetics may be used to block nerves. If performed as a continuous infusion, too much local anesthetic may be infused, with risks of toxicity. However, if the concentration of the local anesthetic is reduced in an effort to prevent toxicity, the nerve block may be inadequate. Therefore, a smart pump that benefits from the observed impedance changes may be created for use in continuous regional anesthesia. In various embodiments, the smart pump may detect if the effect of a local anesthetic is beginning to wear off, and reinstitute the nerve block effects with a single injection at a higher concentration. However, the overall dose delivered to the patient will typically be lower than if continuous infusion is used. In this manner, complications of continuous regional anesthesia may be avoided, and the quality of anesthesia may be improved for the patient.

Figure 14:
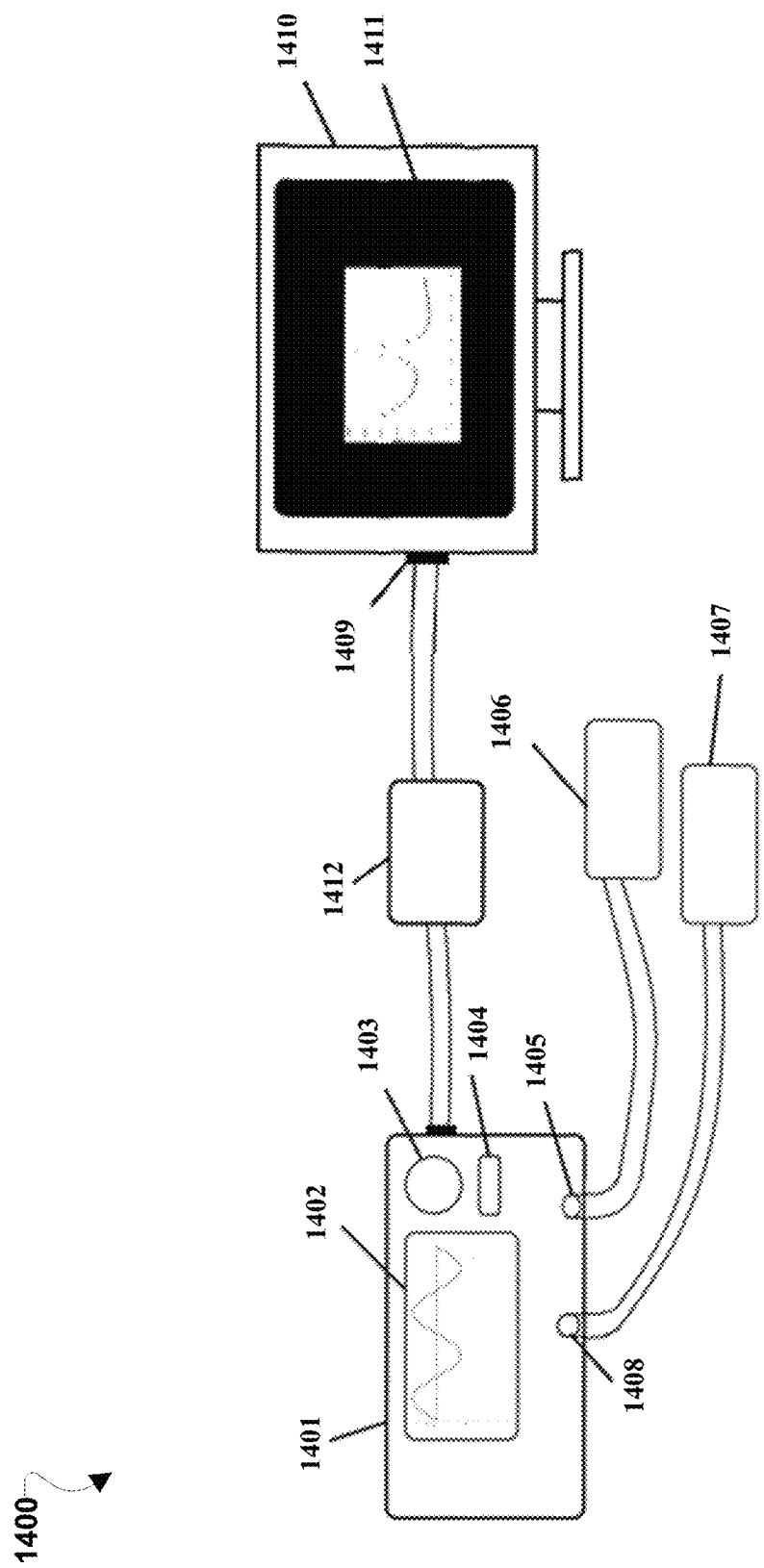
FIG. 14 is an example of a machine configured for waveform application to the nerves for induction of analgesia according to various embodiments.

FIG. 14 illustrates an example of an apparatus or monitoring system for generating nerve resonance according to some embodiments. Such an apparatus 1400 may include a microprocessor-controlled waveform generator 1410, and attached electrodes 1406, 1407. The capturing device 1401 allows a user-determined waveform 1402 to be sent to the patient by electrode cathode 1406 and electrode anode 1407 through ports on the capturing device 1405, 1408. The capturing device (e.g. oscilloscope) may be connected by cable to a waveform generator 1412, which in turn may be connected to a microprocessor-controlled waveform generator 1410 by a USB or other connection 1409. If the electrodes 1406, 1407 are arrays of anodes and cathodes, this waveform generator 1412 may also include a multiplexer (not shown separately). During operation, the applied frequency may be altered by the processor to perform a frequency sweep 1403 while the impedance as a function of frequency is measured by a software system 1411. While the waveform is applied, a single pre-loaded DC pulse may be sent through the processor to the probe 1413 using a waveform sending function 1404.

Figure 15:
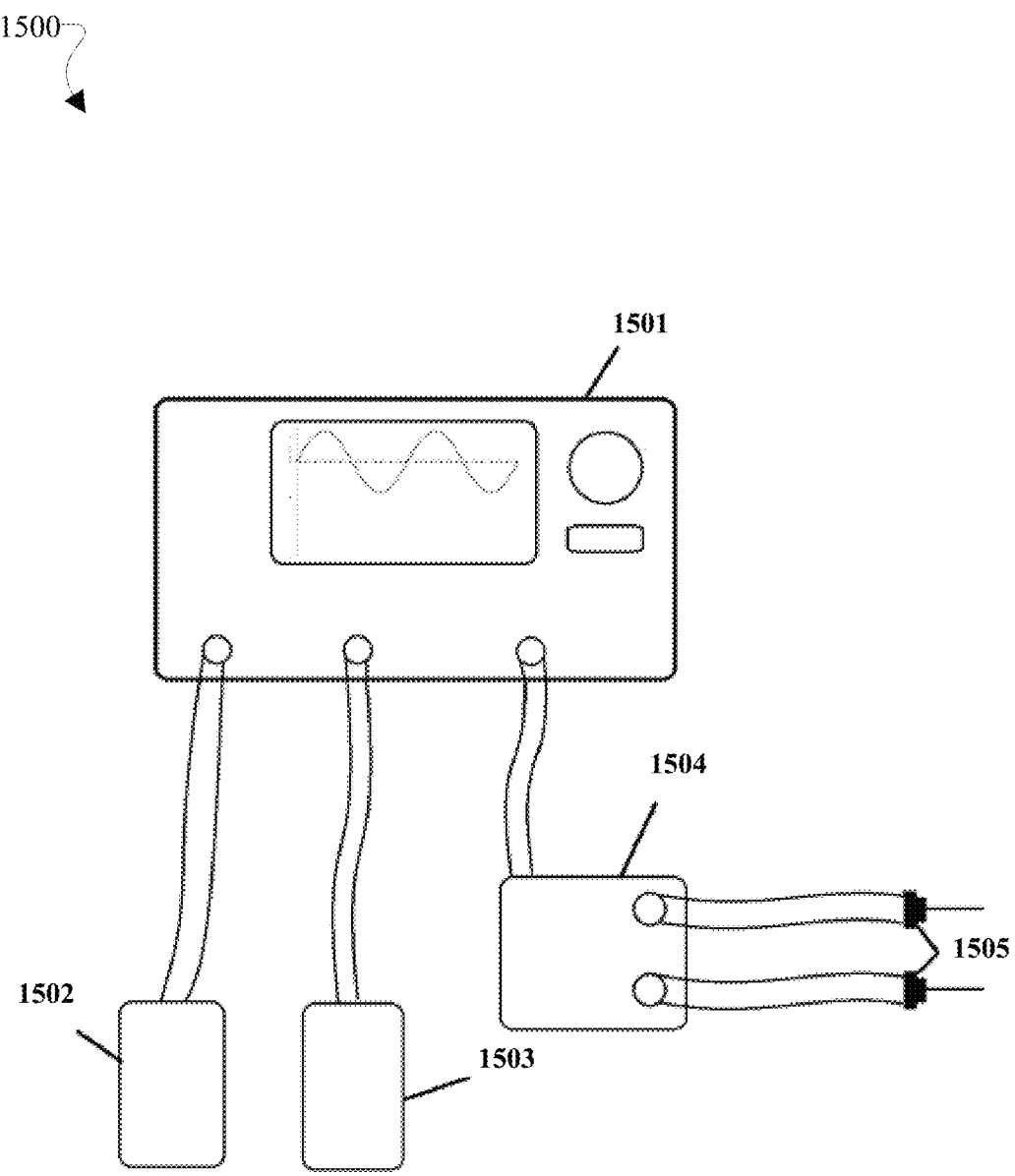
FIG. 15 is an example of the different types of electrodes that may be used for waveform application to the nerves according to various embodiments.

FIG. 15 illustrates an example of the electrodes used for waveform application to the nerves. Electrodes are attached to the capturing device 1501, which sends a user-determined waveform through the electrodes. Electrodes may be single surface cathodal and anodal electrodes or surface array cathodal and anodal electrodes 1502, 1503. Surface array electrodes must be further connected to a multiplexer. Alternatively, a needle probe may be connected to the capturing device 1504. This probe may be connected to needle electrodes 1505 that apply an electric field to the nerves transdermally.

The various embodiments illustrated and described are provided merely as examples to illustrate various features of the claims. However, features shown and described with respect to any given embodiment are not necessarily limited to the associated embodiment and may be used or combined with other embodiments that are shown and described. Further, the claims are not intended to be limited by any one example embodiment.

The foregoing method descriptions and the process flow diagrams are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

In the various embodiments, the wave form, amplitude, and duration of an applied signal may all be controlled by the controller. The controller may also send control signals to the multiplexer to provide the generated waveform to a selected waveform electrode 1 for a predefined period of time (a sampling period). Thus, the duration of the applied waveform may be controlled by the microprocessor via the multiplexer or via the waveform generator. In an embodiment, the controller may direct the waveform generator to produce waveforms of a specified amplitude, frequency, and/or shape, e.g., generating a pulsed train or square waveform, a sinusoidal waveform, a sawtooth waveform, etc.

Alternatively, the controller may instruct the waveform generator, for example in conjunction with the multiplexer, to apply a plurality of different waveforms, each waveform being applied within a sampling time, to an individual waveform electrode prior to switching to another waveform electrode. Complex waveforms, comprising two or more waveforms of different shape and/or frequency, may also be applied in various embodiments.

The multiplexer may be an electronically controlled switch, a multiplexer switching device, a gate array, or any suitable device that may be controlled by the controller to provide current or voltage from the waveform generator to selected, individual electrodes within the waveform electrode array assembly. In an embodiment, the multiplexer may be controlled by the controller to apply the generated waveform to a single waveform electrode, to a selected set of electrodes or to all of the waveform electrodes in the array assembly simultaneously. The waveform generator may also be controlled by the controller in association with the switching device to apply the same current to a plurality of waveform electrodes or all of the waveform electrodes independently of each other simultaneously, even when the waveform electrodes experience or exhibit different impedances. The waveform generator and the switching device may also be controlled by the controller to apply a single current or voltage to all of the waveform electrodes or a plurality of waveform electrodes of the waveform electrode array assembly so that the single current or voltage is dispersed among the selected waveform electrodes. Using software executed by the controller to control the waveform, the applied current or voltage may be varied at an individual sample electrode within the array of electrodes, either during one sampling window or after sampling the other electrodes in the array or in a sequential manner.

A controller in the various embodiment systems may be programmed with software that directs the controller to receive commands from an operator to define the parameters of the waveform, e.g., the shape of the waveform, the positive and negative peak amplitudes, the frequency and the duty cycle. The controller may also contain a memory having stored thereon a plurality of predefined waveforms and may select waveforms to be generated by the waveform generator from the predefined set of waveforms. The waveforms may vary in a number of parameters, including for example bias, positive peak amplitude, minimal amplitude, negative peak amplitude, frequency, shape, and/or duty cycle. Controller may alternatively be configured to receive commands from another controller (e.g., a personal computer) electronically connected to the controller, e.g., by a digital data link as known in the art (e.g., Fire Wire, USB, serial or parallel interface, etc.), or by means of a wireless data link transceiver providing a wireless data link as known in the art (e.g., infrared data (IrDA) serial link, IEEE 802.11g, Bluetooth, or similar) In a further embodiment, the electrode array assembly and controller/signal generator may be configured as a wireless component or module configured so that it may be worn by a patient or placed on a patient at a distance from the host computer. In certain hospital environments where electromagnetic radiation may need to be minimized, a standard infrared data link (IrDA) may be preferred. Using a wireless data link between the electrode array assembly and the controller minimizes the impact on other equipment and attending clinicians.

Sampling of signals in the electrode may be continuous, intermittent or periodic. If continuous, it may be detected as a digital signal e.g., via an analog-to-digital (A/D) converter that converts the received analog signal (e.g., voltage or current) into a digital value by integrating the signal over brief sampling windows as is well known in the art.

Instructions for performing the steps of the methods may be stored in volatile or nonvolatile memory (e.g., PROM or EPROM memory) or on a computer readable medium connected to the controller. A computer readable medium may be any tangible structure, e.g., a magnetic disk, an optical disk, or a magnetic tape; or intangible structure, e.g., a modulated carrier wave containing packetized data, which may be a wireline, optical cable, or a wireless transmission; which is capable of being accessed by a microprocessor or computer. Thus, as used herein, the term "configured to" includes programmed to accomplish or function in the recited manner, as well as physically connected, assembled, wired or otherwise made to accomplish the function.

The controller may be any electronic processing device capable of processing software instructions, receiving data inputs and providing data and command outputs. Examples of suitable processors for use in a system according to the various embodiments include a microprocessor, microcomputer, and microcontroller, as well as external processors/computers, including a personal computer, laptop computer; work station; handheld computer, e.g., a personal data assistant; and combinations or variations of these example processors. A controller or microprocessor may include or be coupled to electronic memory suitable for storing software instructions and data, including volatile and nonvolatile memory as are well known in the art. Data stored in the memory may include the data recorded during operation of the system, and processed data representing tissue discrimination information. The memory may also store data that are useful for operating the system and conducting analysis on measurement data. Data that are useful to an operator for operating the system may include operating instructions, user manuals, trouble-shooting guidance, medical diagnostic guidance, etc.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described generally in terms of functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present claims.

The hardware used to implement the various illustrative logics, logical blocks, modules, and circuits described in connection with the embodiments disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of receiver smart objects, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary embodiments, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable software, which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, FLASH memory, CD-ROM or other optical disk storage, magnetic disk storage or other magnetic storage smart objects, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

While the aforementioned embodiments employ a digital processor to receive and process sensed electrical parameters to determine the desired electrical characteristic, such as impedance, the various embodiments contemplate the use of analog circuit components to accomplish the same functions. For example, while the signal processing algorithms described herein employ digital sampling and curve fitting algorithms, the same functions may be accomplished by a synchronous demodulator such as employing a phased locked loop circuit element. Thus, the various embodiments are not intended to be limited to the digital components and system described in the example embodiments described herein.

The preceding description of the disclosed aspects is provided to enable any person skilled in the art to make or use the claims. Various modifications to these aspects will be readily apparent to those skilled in the art, and the generic principles defined herein may be applied to other aspects and implementations without departing from the scope of the claims. Thus, the present disclosure is not intended to be limited to the aspects and implementations described herein, but is to be accorded the widest scope consistent with the following claims and the principles and novel features disclosed herein.

What is claimed is:

1. A method for inducing analgesia in a localized region of tissue, the method comprising:
   identifying a nerve associated with the localized region;
   determining a resonant frequency for target neuronal cell membranes of the nerve; and
   generating a peripheral nerve blockade using the determined resonant frequency, wherein the resonant frequency comprises a frequency at which impedance of the nerve approaches a maximum; and
   applying the peripheral nerve blockade through electrodes applied to a skin surface in the localized region.

2. The method of claim 1, wherein determining a resonant frequency for target neuronal cell membranes comprises:
   applying, to at least one electrode positioned on the skin surface, a periodic waveform over a range of frequencies, wherein the at least one electrode is attached to a tissue surface in proximity to a section of the nerve;
   measuring impedance of the target neuronal cell membranes throughout the range of frequencies; and
   identifying a peak impedance.

3. The method of claim 2, wherein the resonant frequency for target neuronal cell membranes is within a range of 2-3 kHz or within a range of 12-15 kHz.

4. The method of claim 2, wherein generating the peripheral nerve blockade using the determined resonant frequency comprises:
   applying a fully-rectified, time-variant waveform to the at least one electrode positioned on the skin surface to achieve a voltage gradient across target neuronal cell membranes, wherein the voltage gradient drives a net macro-current across the target neuronal cell membranes; and
   applying a signal at an electrical resonant frequency of the target neuronal membranes to the at least one electrode.

5. The method of claim 2, wherein the at least one electrode positioned on the skin surface is within an array of a plurality of electrodes.

6. A method for achieving a peripheral nerve blockade, the method comprising:
   attaching a plurality of electrodes to a skin surface in proximity to a section of nerve;
   applying a fully-rectified, time-variant waveform to at least one of the plurality of electrodes to achieve a voltage gradient across target neuronal cell membranes, wherein the voltage gradient drives a net macro-current across the target neuronal cell membranes; and
   applying an electrical signal at an electrical resonant frequency of the target neuronal membranes.

7. The method of claim 6, wherein the electrical resonant frequency comprises a frequency at which impedance of the target neuronal membranes is maximized.

8. The method of claim 6, further comprising:
   achieving a central enkephalinergic inhibition of ascending neuronal transmission by constructing a low frequency waveform using components of the electrical resonant frequency of the target neuronal membranes.

9. The method of claim 6, further comprising determining the electrical resonant frequency by:
   applying a periodic waveform to the plurality of electrodes over a range of frequencies;
   measuring impedance of the target neuronal cell membranes throughout the range; and
   identifying a peak impedance.

10. The method of claim 9, wherein the range of frequencies is within 2-5 kHz, wherein the periodic waveform is applied to each of the plurality of electrodes at increments selected from 250 Hz, 100 Hz, or 10 Hz.

11. The method of claim 10, wherein the range of frequencies is within 12-15 kHz, wherein the periodic waveform is applied to each of the plurality of electrodes at increments selected from 250 Hz, 100 Hz, or 10 Hz.

12. A method for maintaining a net macro-current across target neuronal cell membranes within a section of a nerve, the method comprising:
   attaching at least one surface electrode to a skin surface in proximity to the section of the nerve;
   generating a peripheral nerve blockade by applying a fully-rectified, time-variant waveform to the at least one surface electrode such that charge is accumulated by capacitive tissue elements; and
   maintaining the fully-rectified, time-variant waveform for a number of cycles sufficient to achieve a voltage gradient across the membranes, wherein:
      the voltage gradient results in a net macro-current across the membranes; and
      electrical reactance of the membranes is altered.

13. A method for altering a transmembrane voltage gradient of target neurons, the method comprising:
   attaching a plurality of surface electrodes to a skin surface of a patient in proximity to a section of a nerve; and
   generating a peripheral nerve blockade by applying a fully-rectified, time-variant waveform to at least one of the plurality of surface electrodes to achieve a voltage gradient across membranes of the target neurons that results in a net macro-current across the membranes,
   wherein the resting transmembrane voltage gradient is altered during the time that net macro-current is maintained across the membranes.

14. The method of claim 13, wherein the fully-rectified, time-variant waveform has a frequency of less than 3 kilohertz (kHz) such that the net macro-current across the membranes flows from outside the membranes of the target neurons to an axonal path within the nerve.

15. A pain management system, comprising:
   a memory;
   at least one sampling electrode configured to be applied to a skin surface;
   a waveform generator coupled to the at least one sampling electrode;
   at least one return electrode configured to be applied to a skin surface; and a controller coupled to the memory, the waveform generator, and the at least one return electrode, wherein the controller is configured to perform operations comprising:
    detecting a location of a target nerve;
    determining a resonant frequency for neuronal cell membranes of the target nerve; and
    generating a peripheral nerve blockade using the determined resonant frequency, wherein the resonant frequency comprises a frequency at which impedance of a nerve approaches a maximum.

16. The pain management system of claim 15, wherein the controller is further configured to perform operations such that determining a resonant frequency for target neuronal cell membranes comprises:
    applying, to the at least one sampling electrode, a periodic waveform over a range of frequencies;
    measuring impedance of the target neuronal cell membranes throughout the range of frequencies; and
    identifying a peak impedance.

17. The pain management system of claim 16, wherein the resonant frequency for target neuronal cell membranes is within a range of 2-3 kHz or within a range of 12-15 kHz.

18. The pain management system of claim 15, wherein the controller is further configured to perform operations such that generating the peripheral nerve blockade using the determined resonant frequency comprises:
    applying a fully-rectified, time-variant waveform to the at least one sampling electrode to achieve a voltage gradient across target neuronal cell membranes, wherein the voltage gradient drives a net macro-current across the target neuronal cell membranes; and
    applying a signal at an electrical resonant frequency of the target neuronal membranes to the at least one sampling electrode.

* * * * *